(12) United States Patent
Matthews et al.

(10) Patent No.: US 7,291,612 B2
(45) Date of Patent: Nov. 6, 2007

(54) IMMUNOMODULATORY COMPOUNDS

(75) Inventors: Ian Richard Matthews, Abingdon (GB); Thomas Stephen Coutler, Abingdon (GB); Chiara Ghiron, Abingdon (GB); Chris James Brennan, Abingdon (GB); Muhammed Kamal Uddin, Abingdon (GB); Lars Olof Goran Pettersson, Lund (SE); Dorthe da Graca Thrige, Lund (SE); Philip Huxley, Abingdon (GB)

(73) Assignee: Active Biotech A.B., Lund (SE)

( * ) Notice: Subject to any disclaimer, the term of this patent is extended or adjusted under 35 U.S.C. 154(b) by 0 days.

(21) Appl. No.: 11/442,548

(22) Filed: May 30, 2006

(65) Prior Publication Data
US 2006/0217411 A1 Sep. 28, 2006

Related U.S. Application Data

(62) Division of application No. 10/717,519, filed on Nov. 21, 2003, now Pat. No. 7,081,456.
(60) Provisional application No. 60/428,240, filed on Nov. 22, 2002, provisional application No. 60/482,122, filed on Jun. 25, 2003.

(30) Foreign Application Priority Data

Nov. 22, 2002 (SE) .................................. 0203471
May 6, 2003 (SE) .................................. 0301299
Jun. 25, 2003 (SE) .................................. 0301851

(51) Int. Cl.
*C07D 471/06* (2006.01)
*C07D 495/06* (2006.01)
*A61K 31/437* (2006.01)
*A61K 31/4162* (2006.01)
*A61P 37/02* (2006.01)

(52) U.S. Cl. .............................. 514/212.08; 514/232.8; 514/253.03; 514/293; 514/405; 540/524; 544/126; 546/82; 548/359.5

(58) Field of Classification Search ................ 540/524; 544/126; 546/82; 548/359.5; 514/212.08, 514/232.8, 253.03, 293, 405
See application file for complete search history.

(56) References Cited

U.S. PATENT DOCUMENTS

| 4,268,516 | A | 5/1981 | Lombardino et al. |
| 4,312,870 | A | 1/1982 | Yokoyama |
| 4,758,427 | A | * | 7/1988 | Leeson ...................... 514/293 |
| 6,642,249 | B2 | 11/2003 | Bjork et al. |

FOREIGN PATENT DOCUMENTS

| WO | 91/11448 | 8/1991 |
| WO | 91/12255 | 8/1991 |
| WO | 97/34893 | 9/1997 |
| WO | 03/004495 | 1/2003 |

OTHER PUBLICATIONS

L. Savini et al., "High Affinity Central Benzodiazepine Receptor Ligands. Part 2: Quantitative Structure-Activity Relationships and Comparative Molecular Field Analysis of Pyrazolo[4,3-c]quinolin-3-ones", Bioorganic & Medicinal Chemistry, vol. 9, No. 2, Feb. 2001, pp. 431-444.
V. Colotta et al., Tricyclic Heteroaromatic Systems: Synthesis, [3H] Flunitrazepam Brain Membrane Binding Inhibition, and Structure-Activity Relationships of 2,3-Dihydro-2-aryl-4-R-[1]benzopyrano[4,3-c]pyrazole-3-ones, Journal of Pharmaceutical Sciences, vol. 78, No. 3, Mar. 1989, pp. 239-242.
European Search Report dated Jun. 15, 2007.
International Search Report dated Feb. 5, 2004.
David v. Erbe et al., "Small Molecule Ligands Define a Binding Site on the Immune Regulatory Protein B7.1", J. Biol. Chem., vol. 277, Issue 9, 7363-7368, Mar. 1, 2002.

* cited by examiner

*Primary Examiner*—Fiona T. Powers
(74) *Attorney, Agent, or Firm*—Buchanan Ingersoll & Rooney PC

(57) ABSTRACT

The present invention relates to novel heterocyclic compounds, to methods for their preparation, to compositions containing them, and to methods and use for clinical treatment of medical conditions which may benefit from immunomodulation, including rheumatoid arthritis, multiple sclerosis, diabetes, asthma, transplantation, systemic lupus erythematosis and psoriasis. More particularly the present invention relates to novel heterocyclic compounds, which are CD80 antagonists capable of inhibiting the interactions between CD80 and CD28.

19 Claims, No Drawings

IMMUNOMODULATORY COMPOUNDS

This application is a divisional of U.S. Ser. No. 10/717,519, filed Nov. 21, 2003 now U.S. Pat. No. 7,081,456. U.S. Ser. No. 10/717,519 claims the benefit under 35 U.S.C. §119(a)-(d) of Swedish Application No. 0203471-8, filed Nov. 22, 2002, Swedish Application No. 0301299-4, filed May 6, 2003, and Swedish Application No. 0301851-2, filed Jun. 25, 2003, and under 35 U.S.C. §119(e) of U.S. Provisional Application No. 60/428,240, filed Nov. 22, 2002, and U.S. Provisional Application No. 60/482,122, filed Jun. 25, 2003.

FIELD OF THE INVENTION

The present invention relates to novel heterocyclic compounds, to methods for their preparation, to compositions containing them, and to methods and use for clinical treatment of medical conditions which may benefit from immunomodulation, including rheumatoid arthritis, multiple sclerosis, diabetes, asthma, transplantation, systemic lupus erythematosis and psoriasis. More particularly the present invention relates to novel heterocyclic compounds, which are CD80 antagonists capable of inhibiting the interactions between CD80 and CD28.

BACKGROUND OF THE INVENTION

The immune system possesses the ability to control the homeostasis between the activation and inactivation of lymphocytes through various regulatory mechanisms during and after an immune response. Among these are mechanisms that specifically inhibit and/or turn off an immune response. Thus, when an antigen is presented by MHC molecules to the T-cell receptor, the T-cells become properly activated only in the presence of additional co-stimulatory signals. In the absence of accessory signals there is no lymphocyte activation and either a state of functional inactivation termed anergy or tolerance is induced, or the T-cell is specifically deleted by apoptosis. One such co-stimulatory signal involves interaction of CD80 on specialised antigen-presenting cells with CD28 on T-cells, which has been demonstrated to be essential for full T-cell activation. (Lenschow et al. (1996) *Annu. Rev. Immunol.*, 14, 233-258)

A paper by Erbe et al, in J. Biol. Chem. Vol. 277, No. 9, pp 7363-7368 (2002), describes three small molecule ligands which bind to CD80, and inhibit binding of CD80 to CD28 and CTLA4. Two of the disclosed ligands are fused pyrazolones of structures A and B:

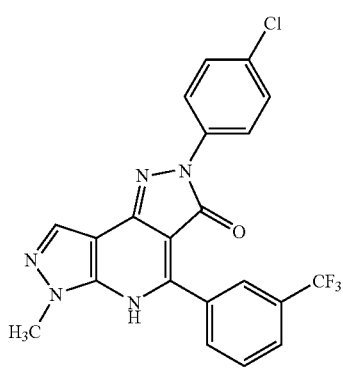

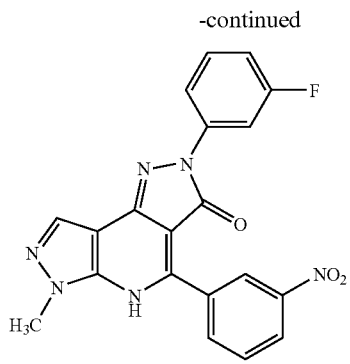

DESCRIPTION OF THE INVENTION

According to the present invention there is provided a compound of formula (I) or a pharmaceutically or veterinarily acceptable salt thereof:

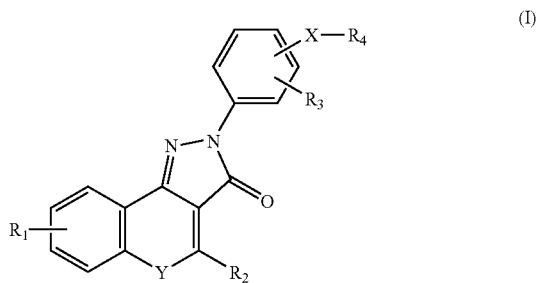

wherein
$R_1$ and $R_3$ independently represent H; F; Cl; Br; —$NO_2$; —CN; $C_1$-$C_6$ alkyl optionally substituted by F or Cl; or $C_1$-$C_6$ alkoxy optionally substituted by F;
$R_2$ represents H, or optionally substituted $C_1$-$C_6$ alkyl, $C_3$-$C_7$ cycloalkyl or optionally substituted phenyl;
Y represents —O—, —S—, N-oxide, or —N($R_5$)— wherein $R_5$ represents H or $C_1$-$C_6$ alkyl;
X represents a bond or a divalent $C_1$-$C_6$ alkylene radical;
$R_4$ represents —C(=O)N$R_6R_7$, —N$R_7$C(=O)$R_6$, —N$R_7$C(=O)O$R_6$, —NHC(=O)NH$R_6$, or —NHC(=S) NH$R_6$ wherein
$R_6$ represents H, or a radical of formula —(Alk)$_b$-Q wherein b is 0 or 1, and
Alk is an optionally substituted divalent straight chain or branched $C_1$-$C_{12}$ alkylene, $C_2$-$C_{12}$ alkenylene or $C_2$-$C_{12}$ alkynylene radical which may be interrupted by one or more non-adjacent —O—, —S— or —N($R_8$)— radicals wherein $R_8$ represents H or $C_1$-$C_4$ alkyl, $C_3$-$C_4$ alkenyl, $C_3$-$C_4$ alkynyl, or $C_3$-$C_6$ cycloalkyl, and
Q represents H; —$CF_3$; —OH; —SH; —N$R_8R_8$ wherein each $R_8$ may be the same or different; an ester group; or an optionally substituted phenyl, $C_3$-$C_7$ cycloalkyl, $C_5$-$C_7$ cycloalkenyl or heterocyclic ring having from 5 to 8 ring atoms; and
$R_7$ represents H or $C_1$-$C_6$ alkyl; or when taken together with the atom or atoms to which they are attached $R_6$ and $R_7$ form an optionally substituted heterocyclic ring having from 5 to 8 ring atoms.

Compounds of general formula (I) are CD80 antagonists. They inhibit the interaction between CD80 and CD28 and thus the activation of T cells, thereby modulating the immune response.

Accordingly the invention also includes:

(i) a compound of formula (I) or a pharmaceutically or veterinarily acceptable salt thereof for use in the treatment of conditions which benefit from immunomodulation.

(ii) the use of a compound of formula (I) or a pharmaceutically or veterinarily acceptable salt thereof in the manufacture of a medicament for the treatment of conditions which benefit from immunomodulation,.

(iii) a method of immunomodulation in humans and non-human primates, comprising administration to a subject in need of such treatment an immunomodulatory effective dose of a compound of formula (I) or a pharmaceutically or veterinarily acceptable salt thereof.

(iv) a pharmaceutical or veterinary composition comprising a compound of formula (I) or a pharmaceutically or veterinarily acceptable salt thereof together with a pharmaceutically or veterinarily acceptable excipient or carrier.

Conditions which benefit from immunomodulation include:
Adrenal insufficiency
Allergic angiitis and granulomatosis
Amylodosis
Ankylosing spondylitis
Asthma
Autoimmune Addison's disease
Autoimmune alopecia
Autoimmune chronic active hepatitis
Autoimmune hemolytic anemia
Autoimmune neutropenia
Autoimmune thrombocytopenic purpura
Autoimmune vasculitides
Behcet's disease
Cerebellar degeneration
Chronic active hepatitis
Chronic inflammatory demyelinating polyradiculoneuropathy
Dermatitis herpetiformis
Diabetes
Eaton-Lambert myasthenic syndrome
Encephalomyelitis
Epidermolysis bullosa
Erythema nodosa
Gluten-sensitive enteropathy
Goodpasture's syndrome
Graft versus host disease
Guillain-Barre syndrome
Hashimoto's thyroiditis
Hyperthyrodism
Idiopathic hemachromatosis
Idiopathic membranous glomerulonephritis
Minimal change renal disease
Mixed connective tissue disease
Multifocal motor neuropathy
Multiple sclerosis
Myasthenia gravis
Opsoclonus-myoclonus syndrome
Pemphigoid
Pemphigus
Pernicious anemia
Polyarteritis nodosa
Polymyositis/dermatomyositis
Post-infective arthritides
Primary biliary sclerosis
Psoriasis
Reactive arthritides
Reiter's disease
Retinopathy
Rheumatoid arthritis
Sclerosing cholangitis
Sjögren's syndrome
Stiff-man syndrome
Subacute thyroiditis
Systemic lupus erythematosus
Systemic sclerosis (scleroderma)
Temporal arteritis
Thromboangiitis obliterans
Transplantation rejection
Type I and type II autoimmune polyglandular syndrome
Ulcerative colitis
Uveitis
Wegener's granulomatosis As used herein the term "alkylene" refers to a straight or branched alkyl chain having two unsatisfied valencies, for example —$CH_2$—, —$CH_2CH_2$—, —$CH_2CH_2CH_2$—, —$CH(CH_3)CH_2$—, —$CH(CH_2CH_3)CH_2CH_2CH_3$, and —$C(CH_3)_3$.

As used herein the term "heteroaryl" refers to a 5- or 6-membered aromatic ring containing one or more heteroatoms. Illustrative of such groups are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl.

As used herein the unqualified term "heterocyclyl" or "heterocyclic" includes "heteroaryl" as defined above, and in particular means a 5-8 membered aromatic or nonaromatic heterocyclic ring containing one or more heteroatoms selected from S, N and O, including for example, pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzofuranyl, pyranyl, isoxazolyl, quinuclidinyl, aza-bicyclo[3.2.1]octanyl, benzimidazolyl, methylenedioxyphenyl, maleimido and succinimido groups.

Unless otherwise specified in the context in which it occurs, the term "substituted" as applied to any moiety herein means substituted with one or more of the following substituents, namely ($C_1$-$C_6$)alkyl, trifluoromethyl, ($C_1$-$C_6$)alkoxy (including the special case where a ring is substituted on adjacent ring C atoms by methylenedioxy or ethylenedioxy), trifluoromethoxy, ($C_1$-$C_6$)alkylthio, phenyl, benzyl, phenoxy, ($C_3$-$C_8$)cycloalkyl, hydroxy, mercapto, amino, fluoro, chloro, bromo, cyano, nitro, oxo, —COOH, —$SO_2OH$, —$CONH_2$, —$SO_2NH_2$, —$COR^A$, —$COOR^A$, —$SO_2OR^A$, —$NHCOR^A$, —$NHSO_2R^A$, —$CONHR^A$, —$SO_2NHR^A$, —$NHR^A$, —$NR^AR^B$, —$CONR^AR^B$ or —$SO_2NR^AR^B$ wherein $R^A$ and $R^B$ are independently a ($C_1$-$C_6$)alkyl group. In the case where "substituted" means substituted by ($C_3$-$C_8$)cycloalkyl, phenyl, benzyl or phenoxy, the ring thereof may itself be substituted with any of the foregoing, except ($C_3$-$C_8$)cycloalkyl phenyl, benzyl or phenoxy.

As used herein the unqualified term "carbocyclyl" or "carbocyclic" refers to a 5-8 membered ring whose ring atoms are all carbon.

Some compounds of the invention contain one or more chiral centres because of the presence of asymmetric carbon atoms. The presence of asymmetric carbon atoms gives rise to stereoisomers or diastereoisomers with R or S stereochemistry at each chiral centre. The invention includes all such stereoisomers and diastereoisomers and mixtures thereof.

Salts of salt forming compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates; and base addition salts, for example sodium, potassium, magnesium, and calcium salts. Where the compound contains an amino group, quaternary amino salts are also feasable, and are included in the invention.

In the compounds of the invention the following are examples of the several structural variables:

$R_1$ may be, for example, H, F, Cl, methyl, methoxy, or methylenedioxy. Currently it is preferred that $R_1$ is H, Cl or especially F;

$R_2$ may be, for example H, methyl, methoxy, cyclopropyl, phenyl, or fluoro-, chloro-, methyl, or methoxy-substituted phenyl. H or cyclopropyl is presently preferred;

$R_3$ may be, for example, H, F, Cl, methyl, methoxy, or methylenedioxy. Currently it is preferred that $R_3$ is F or Cl, and it is most preferred that $R_3$ be H;

Y may be, for example, —O—, —S—, or —N($R_5$)— wherein $R_5$ represents H or methyl. —NH— or —S— is presently preferred.

X may be, for example a bond, or a —$CH_2$— or —$CH_2CH_2$— radical. A bond is presently preferred.

$R_4$ represents —C(=O)$NR_6R_7$, —$NR_7$C(=O)$R_6$, —$NR_7$C(=O)$OR_6$, —NHC(=O)$NHR_6$, or —NHC(=S) $NHR_6$. Of these —$NR_7$C(=O)$R_6$, and especially —C(=O) $NR_6R_7$ and —NHC(=O)$NHR_6$ are curently preferred. $R_7$ is preferably H, but a wide range of $R_6$ substituents have given rise to highly active compounds of the invention. Many exemplary $R_6$ substituents appear in the compounds of the Examples below.

$R_6$ may be, for example, H or a radical of formula —$Alk_b$-Q wherein b is 0 or 1 and Alk may be, for example a —$(CH_2)_n$—, —CH(($CH_2$) $CH_3$)($CH_2$)$_n$—, —C(($CH_2$)$_m$$CH_3$)(($CH_2$)$_p$$CH_3$)($CH_2$)$_n$, —($CH_2$)$_n$—O—($CH_2$)$_m$—, —($CH_2$)$_n$—NH—($CH_2$)$_m$—, or —($CH_2$)$_n$—NH—($CH_2$)$_n$—NH—($CH_2$)$_p$— radical where n is 1, 2, 3 or 4 and m and p are independently 0, 1, 2, 3 or 4, and Q may represent H, —OH, —$COOCH_3$, phenyl, cyclopropyl, cyclopentyl, cyclohexyl, pyridyl, furyl, thienyl, or oxazolyl; and $R_7$ may be, for example, H, or when taken together with the atom or atoms to which they are attached $R_6$ and $R_7$ may form a heterocyclic ring of 5, 6 or 7 members.

Specific examples of $R_4$ groups include those present in the compounds of the Examples herein.

Compounds of the invention may be prepared by synthetic methods known in the literature, from compounds which are commercially available or are accessible from commercially available compounds. For example, compounds of formula (I) wherein $R_4$ is a group —$NR_7$C(=O) $R_6$ may be prepared by acylation of an amine of formula (II) with an acid chloride of formula (III):

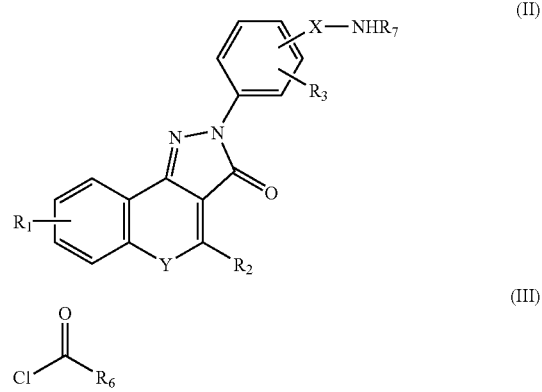

Compounds of the invention wherein $R_4$ is a group —NHC(=O)$NHR_6$ may be prepared by reaction of an amine of formula (IIA) with an isocyanate of formula (IIIA)

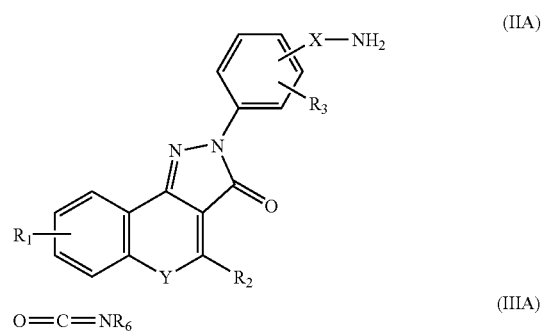

Compounds of the invention wherein $R_4$ is a group —C(=O)$NHR_6$ may be prepared by reaction of an acid chloride of formula (IIB) with an amine $NHR_6R_7$:

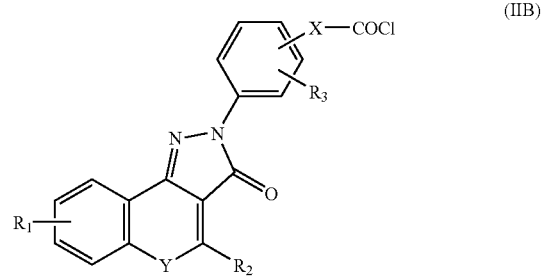

Compounds of the invention wherein $R_4$ is a group —$NR_7$C(=O)$OR_6$ may be prepared by reaction of an amine of formula (II) with a chloroformate ClC(=O)$OR_6$.

The following Examples illustrate the preparation of compounds of the invention:

Preparation of Intermediate 1

2-(4-Nitrophenyl)-6-fluoro-2,5-dihydropyrazolo[4,3-c]-quinolin-3-one

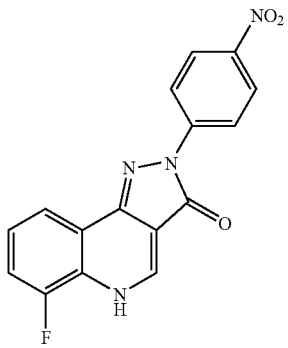

4-Nitrophenylhydrazine (2.28 g, 0.014 mol) was added in one portion to a stirred solution of 4-chloro-8-fluoro-quinoline-3-carboxylic acid ethyl ester (3.58 g, 0.014 mol) in anhydrous n-butyl alcohol (50 ml) at room temperature. The mixture was refluxed for 16 h under nitrogen, cooled to room temperature and then filtered to leave an orange solid. The solid was purified by washing sequentially with ethyl acetate (20 ml) and heptane (20 ml) and then finally dried under suction to give the pyrazolone (3.93 g, 87%) as a dark orange solid, LCMS m/z 325.24 [M+H]$^+$ @ $R_T$ 1.47 min.

Preparation of Intermediate 2

2-(4-Aminophenyl)-6-fluoro-2,5-dihydropyrazolo[4,3-c]-quinolin-3-one

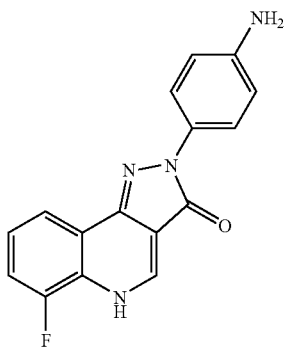

Tin (II) chloride dihydrate (12.5 g, 0.055 mol) was added in one portion to a stirred solution of 2-(4-nitrophenyl)-6-fluoro-2,5-dihydro-pyrazolo[4,3-c]quinolin-3-one (intermediate 1) (3.59 g, 0.011 mol) in ethyl alcohol (110 ml) at room temperature. The mixture was then heated to 80° C. for 8 h, cooled to room temperature and filtered to leave a yellow solid. The solid was suspended in a biphasic solution of ethyl acetate (1L), a saturated solution of Rochelles salt (500 ml) and a saturated solution of sodium bicarbonate (500 ml) and stirred at room temperature for 2 h. The mixture was filtered and the remaining solid was washed with water and dried under vacuum to afford the title compound (3.39 g, 99%) as a bright yellow solid, LCMS m/z 295.30 [M+H]$^+$ @ $R_T$ 0.84 min.

EXAMPLE 1

N-[4-(6-Fluoro-3-oxo-3,5-dihydropyrazolo[4,3-c]quinolin-2-yl)-phenyl]-2-methyl-butyramide

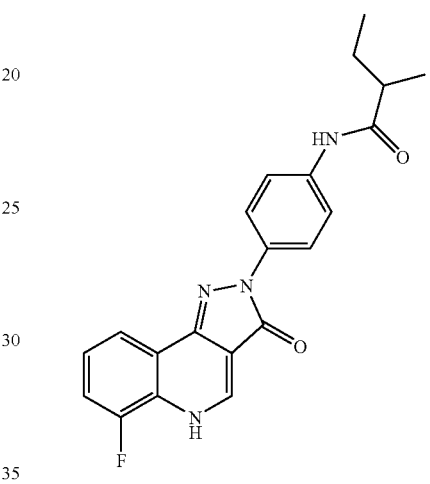

(±)-2-Methylbutyryl chloride (13.6 μl, 0.11 mmol) was added dropwise over 30 sec to a stirred solution of 2-(4-amino-phenyl)-6-fluoro-2,5-dihydro-pyrazolo[4,3-c]quinolin-3-one (Intermediate 2) (30 mg, 0.10 mmol), triethylamine (14 μl, 0.11 mmol) and 4-dimethylaminopyridine (2.4 mg, 0.02 mmol) in dichloromethane (1 ml) at room temperature. The mixture was stirred at room temperature for 16 h. The yellow solid was then filtered and purified by washing sequentially with a saturated solution of sodium bicarbonate (1 ml), ethyl acetate (1 ml) and ethyl alcohol (0.5 ml) and finally dried under suction to give the title compound (10 mg, 26%) as a bright yellow solid, LCMS m/z 379.36 [M+H]$^+$ @ $R_T$ 1.18 min. $\delta_H$(400 MHz, (CD$_3$)$_2$SO) 9.89 (1H, s), 8.52 (1H, s), 8.15 (2H, d J 9.0 Hz), 8.01 (1H, d J 7.0 Hz), 7.69 (2H, d J 9.0 Hz) 7.57-7.46 (2H, m), 2.46-2.39 (1H, m), 1.69-1.36 (2H, m), 1.11 (3H, d J 6.8 Hz), 0.91(3H, t J 7.3 Hz).

The title compound, and compounds of subsequent Examples, were tested in the assay described below in the Assay Section, to determine their activities as inhibitors of the CD80-CD28 interaction. The present title compound had an activity rating of ***.

EXAMPLES 2-49

The following compounds were synthesized by the route described in Example 1, substituting the appropriate acid chloride for (±)-2-methylbutyryl chloride:

EXAMPLE 2

2-Methyl-pentanoic acid [4-(6-fluoro-3-oxo-3,5-dihydro-pyrazolo[4,3-c]quinolin-2-yl)-phenyl]-amide

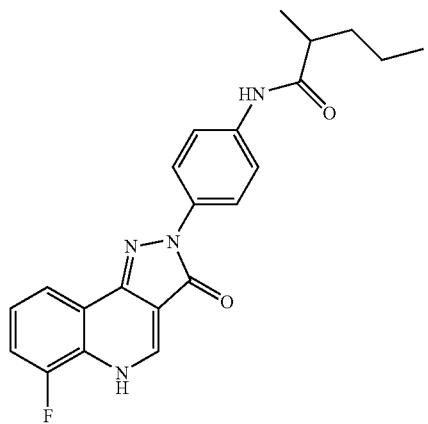

$\delta_H$(400 MHz, (CD$_3$)$_2$SO) 9.92 (1H, s), 8.53 (1H, s), 8.12 (2H, d J 9.2 Hz), 8.05 (1H, d J 7.6 Hz), 7.70 (2H, d J 9.2 Hz), 7.63-7.53 2H, m), 1.68-1.58 (1H, m), 1.38-1.28 (3H, m), 1.11 (3H, d J 6.6 Hz), 0.91 (3H, t J 7.1 Hz).

Activity ***

EXAMPLE 3

1-Methyl-1H-pyrrole-2-carboxylic acid [4-(6-fluoro-3-oxo-3,5-dihydro-pyrazolo[4,3-c]quinolin-2-yl)-phenyl]-amide

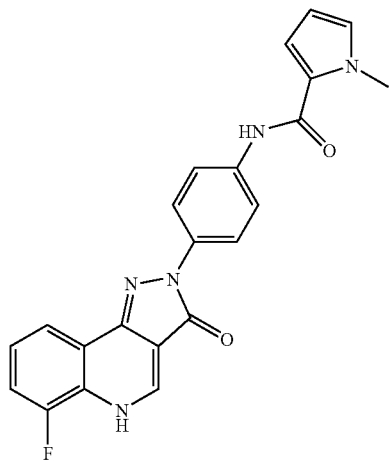

$\delta_H$(400 MHz, (CD$_3$)$_2$SO) 9.76 (1H, s), 8.50 (1H, s), 8.26 (2H, d 9.0 Hz), 7.97-7.94 (1H, m), 7.73 (2H, d J 9.0 Hz), 7.39-7.28 (2H, m), 7.07-7.01 (2H, m), 3.91 (3H, s).

Activity *

EXAMPLE 4

N-[4-(6-Fluoro-3-oxo-3,5-dihydro-pyrazolo[4,3-c]quinolin-2-yl)-phenyl]-3-methyl-butyramide

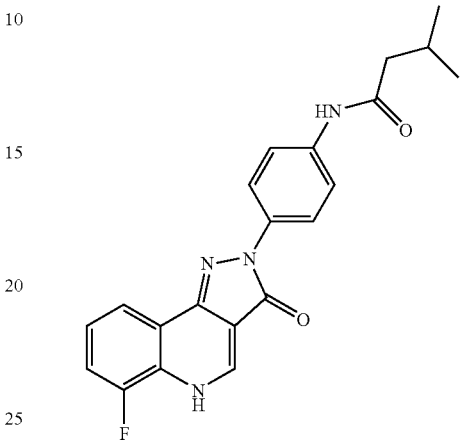

$\delta_H$(400 MHz, (CD$_3$)$_2$SO) 9.92 (1H, s), 8.52 (1H, s), 8.14 (2H, d J 9.2 Hz), 8.01 (1H, d J 7.3 Hz), 7.67 (2H, d J 9.2 Hz), 7.57-7.47 (2H, m), 2.21 (2H, d J 6.8 Hz), 2.14-2.07 (1H, m), 0.96 (6H, d J 6.6 Hz).

Activity **

EXAMPLE 5

2-Propyl-pentanoic acid [4-(6-fluoro-3-oxo-3,5-dihydro-pyrazolo[4,3-c]quinolin-2-yl)-phenyl]-amide

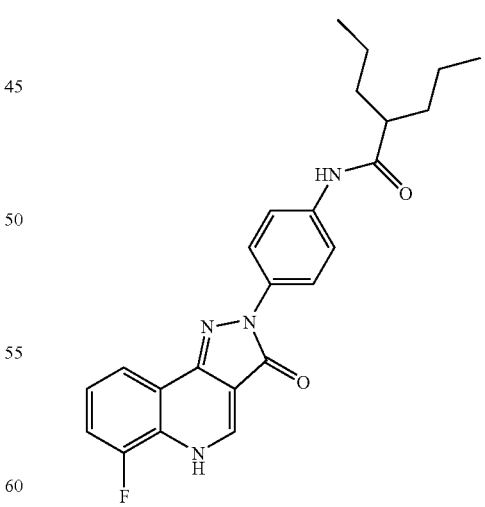

$\delta_H$(400 MHz, (CD$_3$)$_2$SO) 9.93 (1H, s), 8.53 (1H, s), 8.11 (2H, d J 9.0 Hz), 8.05 (1H, d J 7.8 Hz), 7.70 (2H, d J 9.0 Hz), 7.59-7.46 (2H, m), 2.46-2.35 (1H, m), 1.63-1.27 (4H, m), 0.90 (6H, t J 7.1 Hz).

Activity *

EXAMPLE 6

5-[4-(6-Fluoro-3-oxo-3,5-dihydro-pyrazolo[4,3-c]quinolin-2-yl) phenylcarbamoyl]-pentanoic acid methyl ester

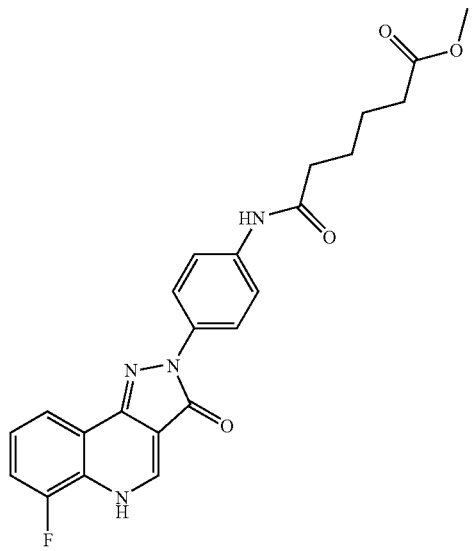

δ$_H$(400 MHz, (CD$_3$)$_2$SO) 9.85 (1H, s), 8.47 (1H, s), 8.25 (2H, d J 9.0 Hz), 7.91-7.90 (1H, m), 7.59 (2H, d J 9.0 Hz), 7.29-7.20 (2H, m), 3.61 (3H, s), 2.38-2.28 (4H, m), 1.64-1.50 (4H, m).

Activity ***

EXAMPLE 7

N-[4-(6-Fluoro-3-oxo-3,5-dihydro-pyrazolo[4,3-c]quinolin-2-yl)-phenyl]-2,2-dimethyl-propionamide

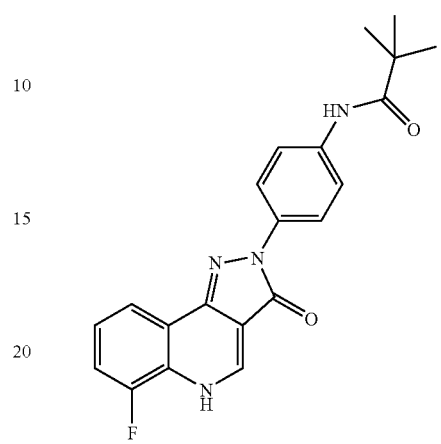

δ$_H$(400 MHz, (CD$_3$)$_2$SO) 9.26 (1H, s), 8.52 (1H, s), 8.15 (2H, d J 9.2 Hz), 8.03 (1H, d J 8.8 Hz), 7.71 (2H, d J 9.2 Hz), 7.56-7.47 (2H, m), 1.26 (9H, s).

Activity **

Examples 8 to 28 were also prepared by the method of Example 1 using the appropriate acid chloride:

| Example | X | R | M.S. (MH+) | Activity |
|---|---|---|---|---|
| 8 | 6-F | ![structure: -C(CH3)2-CH2-O-CH2-phenyl] | 443.4 | ** |
| 9 | 6-F | —CH$_2$Cl | 371.31 | ** |
| 10 | 6-F | ![structure: -C(CH3)2-furan-2-yl] | 389.34 | * |

-continued
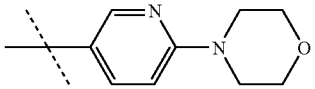
| Example | X | R | M.S. (MH+) | Activity |
|---|---|---|---|---|
| 11 | 6-F | 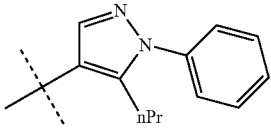 | 485.45 | * |
| 12 | 6-F | CO₂Me | 381.34 | ** |
| 13 | 6-F | OEt | 367.18 | |
| 14 | 6-F | 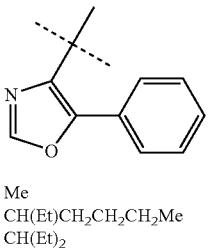 | 507.43 | * |
| 15 | 6-F | 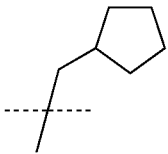 | 466.41 | ** |
| 16 | 6-F | Me | 337.36 | ** |
| 17 | 6-F | CH(Et)CH₂CH₂CH₂Me | 421.46 | * |
| 18 | 6-F | CH(Et)₂ | 393.41 | *** |
| 19 | 6-F | 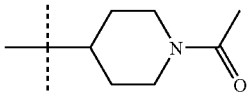 | 405.41 | ** |
| 20 | 6-F | 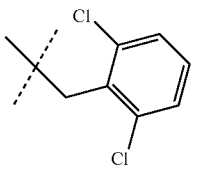 | 448.44 | ** |
| 21 | 6-F | 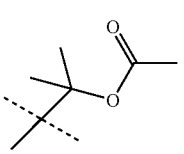 | 481.35 | ** |
| 22 | 6-F |  | 423.42 | *** |

-continued
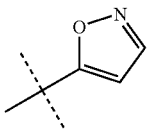
| Example | X | R | M.S. (MH+) | Activity |
|---|---|---|---|---|
| 23 | 6-F | (CH₂)₈CO₂Me | 493.51 | ** |
| 24 | 6-F | iPr | 365.36 | *** |
| 25 | 6-F | CH₂OCH₂CH₂OMe | 411.4 | ** |
| 26 | 6-F | CH(Me)(nPr) | 393.42 | *** |
| 27 | 6-F | CH₂OMe | 367.24 | ** |
| 28 | 6-F | 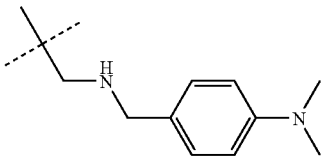 | 390.33 | ** |
| 29 | 6-F | CH₂CH₂CH₂N⁺(Me)₃ | 422.1 (M+) | *** |
| 30 | 6-F | CH₂CH₂CH₂N(Me)₂ | 408.3 | *** |
| 31 | 6-F | CH₂NHCH₂CH₂CH₂N(Me)(Ph) | 499.3 | * |
| 32 | 6-F | 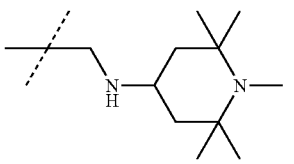 | 485.3 | * |
| 33 | 6-F | 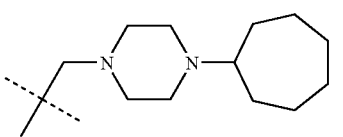 | 505.1 | *** |
| 34 | 6-F | 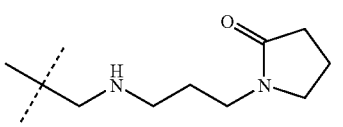 | 517.2 | *** |
| 35 | 6-F | 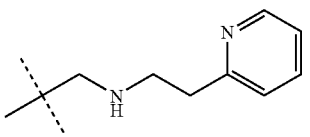 | 477.1 | *** |
| 36 | 6-F |  | 457.1 | ** |

-continued
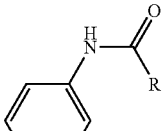
| Example | X | R | M.S. (MH+) | Activity |
|---|---|---|---|---|
| 37 | 6-F | 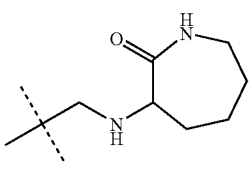 | 463.1 | ** |
| 38 | 6-F | 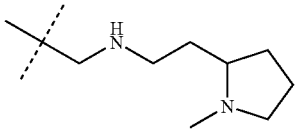 | 438.3 | ** |
| 39 | 6-F | 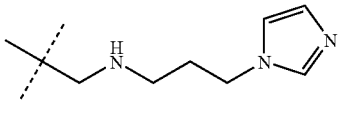 | 463.2 | *** |
| 40 | 6-F | 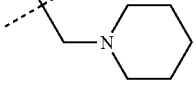 | 460.4 | ** |
| 41 | 6-F | CH$_2$NHCH$_2$CH$_2$N(iPr)$_2$ | 479.4 | ** |
| 42 | 6-F | 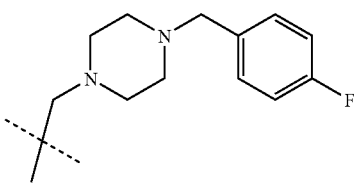 | 420.2 | ** |
| 43 | H | CH(NH$_2$)CH$_3$ | 348.3 | ** |
| 44 | H | CH(Me)nPr | 375.3 | * |
| 45 | H | iPr | 347.3 | ** |
| 46 | 6-F | CH(NH$_2$)CH$_3$ | 366.3 | *** |
| 47 | H | CH(Me)Et | 361.3 | ** |
| 48 | 6-F |  | 529.1 | ** |
| 49 | 6-F | CH$_2$N(Me)CH$_2$Ph | 456.4 | ** |

Preparation of Intermediate 3

3-(6-Fluoro-3-oxo-3,5-dihydro-pyrazolo[4,3-c]quinolin-2-yl)-benzoic acid

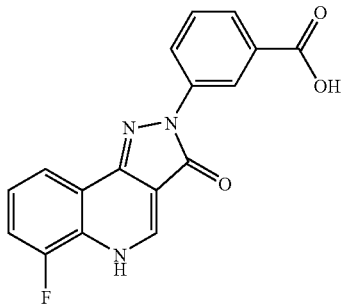

3-Hydrazinobenzoic acid (1.91 g, 0.013 mol) was added in one portion to a stirred solution of 4-chloro-8-fluoro-quinoline-3-carboxylic acid ethyl ester (2.93 g, 0.011 mol) in n-butanol (60 ml) at room temperature. The solution was heated to reflux for 16 h, cooled to room temperature and the resulting yellow solid filtered, washed with tert-butyl methyl ether and then dried. The solid was redissolved in a solution of tetrahydrofuran water (2:1; 21 ml) and lithium hydroxide (1.27 g, 0.031 mol) was then added. After stirring at room temperature for 16 h, concentrated hydrochloric acid (3 ml) was added dropwise to the mixture to precipitate a yellow solid which was filtered and dried under vacuum to give the title compound (intermediate 3) (2.32 g, 63%) as a bright yellow solid.

Preparation of Intermediate 4

3-(6-Fluoro-3-oxo-3,5-dihydro-pyrazolo[4,3-c]quinolin-2-yl)-benzoyl chloride

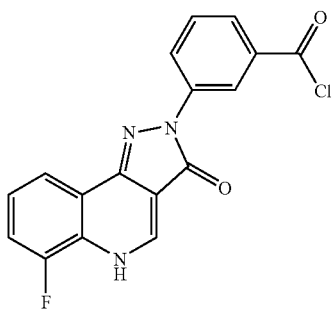

Oxalyl chloride (20 ml, 0.2 mol) was added dropwise over 2 min to a stirred solution of 3-(6-fluoro-3-oxo-3,5-dihydro-pyrazolo[4,3-c]quinolin-2-yl)-benzoic acid (intermediate 3) (2.0 g, 6.1 mmol) in dichloromethane (10 ml) at room temperature. N,N-Dimethylformamide (50 µl) was then added and the resulting mixture heated to 50° C. for 1 h. The solution was then cooled to room temperature and then concentrated in vacuo to leave the title compound (intermediate 4) (2.0 g, 96%) as a beige solid.

EXAMPLE 50

3-(6-Fluoro-3-oxo-3,5-dihydro-pyrazolo[4,3-c]quinolin-2-yl)-N-(3-methoxy-propyl)-benzamide

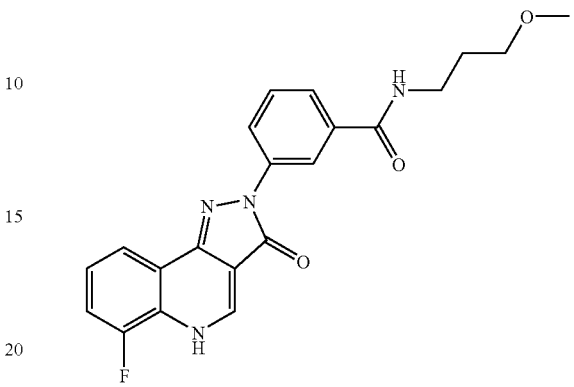

3-Methoxypropylamine (0.026 g, 0.29 mmol) was added to a stirred solution of 3-(6-fluoro-3-oxo-3,5-dihydro-pyrazolo[4,3-c]quinolin-2-yl)-benzoyl chloride (intermediate 4) (26 mg 0.29 mmol) in tetrahydrofuran (2 ml) and the mixture stirred at room temperature for 15 min. Triethylamine (0.2 ml, 1.4 mmol) was then added and the resulting mixture stirred overnight. 1M Hydrochloric acid (3-4 ml) was added dropwise to precipitate a yellow solid which was filtered and dried under suction to give the amide (79 mg, 0.20 mmol) as a yellow solid, LCMS m/z 395.25 [M+H]$^+$ @ $R_T$ 1.04 min; $\delta_H$(400 MHz, (CD$_3$)$_2$SO) 8.59 (1H, m), 8.57 (1H, s), 8.39 (1H, app d J 9.3 Hz), 8.08 (1H, app d J 7.3 Hz), 7.66-7.53 (5H, m), 3.37-3.33 (4H, m), 3.27 (3H, s), 1.83-1.77 (2H, m).

Activity **

EXAMPLE 51

N-Ethyl-3-(6-fluoro-3-oxo-3,5-dihydro-pyrazolo[4,3-c]-quinolin-2-yl)-benzamide

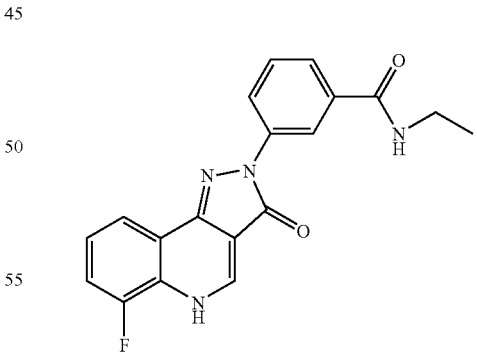

Prepared by the method of Example 53 substituting ethylamine for 3-methoxypropylamine.

$\delta_H$(400 MHz, (CD$_3$)$_2$SO) major rotomer quoted; 8.56 (1H, br s), 8.47 (1H, m), 8.21 (2H, d J 8.5 Hz), 7.94 (2H, d J 8.5 Hz), 3.96 (3H, s), 3.31 (2H, q J 7.3 Hz), 2.58 (3H, s), 1.15 (3H, t J 7.4 Hz).

Activity **

EXAMPLE 52

N-Benzyl-3-(6-fluoro-3-oxo-3,5-dihydro-pyrazolo[4,3-c]-quinolin-2-yl)-benzamide

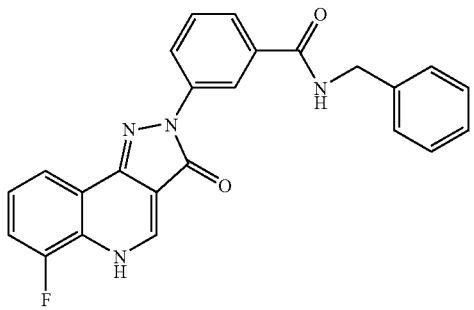

Prepared by the method of Example 53 substituting benzylamine for 3-methoxypropylamine.

LCMS m/z 427.16 $[M+H]^+$ @ $R_T$ 1.28 min.

Activity *

Examples 53 to 64 were prepared by the method of example 50, using the appropriate amine.

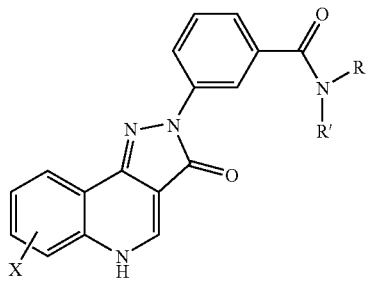

| Example | X | R | R' | M.S. (MH+) | Activity |
|---|---|---|---|---|---|
| 53 | 6-F | $CH_2CH_2CH_2N(Me)_2$ | Me | 422.5 | * |
| 54 | 6-F | $CH_2CH_2CH_2N(Me)_2$ | H | 408.4 | ** |
| 55 | 6-F | (trans-4-aminocyclohexyl) | H | 420.4 | * |
| 56 | 6-F | (pyrrolidinyl-propyl) | H | 434.4 | * |
| 57 | 6-F | (pyrrolidinyl-butyl) | H | 448.4 | ** |
| 58 | 6-F | $CH_2CH_2CH_2CH_2N(Me)_2$ | H | 422.4 | ** |
| 59 | 6-F | $CH_2CH_2OMe$ | H | 381.3 | ** |
| 60 | 6-F | Et | Et | 379.3 | * |
| 61 | 6-F | $CH_2CO_2Me$ | H | 395.2 | * |
| 62 | 6-F | $CH_2CCH$ | H | 361.3 | ** |
| 63 | 6-F | CH2Ph | Me | 427.2 | ** |
| 64 | 6-F | (4-ethoxycarbonylpiperidinyl) | | 463.3 | * |

EXAMPLE 65

N-(3-Dimethylamino propyl)-4-(4-cyclopropyl-3-oxo-3,5-dihydro-pyrazolo[4,3-c]quinolin-2-yl]-benzamide

Step 1

2-cyclopropyl-4-oxo-1,4-dihydro-quinoline-3-carboxylic acid ethyl ester

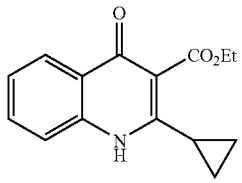

A solution of 3-cyclopropyl-3-oxo-propionic acid methyl ester (6.2 g, 0.038 mols), 2-amino benzoic acid ethyl ester (4.95 g, 0.03 mols) and p-toluene sulfonic acid (0.04 g, 0.2 mmols) in toluene (25 ml) was heated at 125° C. for 2 h; 15 ml of solvent was then distilled. To the residual orange solution was added sodium ethoxide (2 M, 15 ml) in ethanol (reaction mixture turns red). This red mixture was stirred at 120° C. for 2 h; 15 ml of solvent was again distilled. The reaction mixture was left to cool to room temperature, diluted with ethyl acetate (1 litre), extracted with HCl 0.1 M and water. The combined organic extracts were dried over sodium sulfate and concentrated in vacuo to leave an orange residue which was washed once with cold ethyl acetate to yield 2-cyclopropyl-4-oxo-1,4-dihydro-quinoline-3-carboxylic acid ethyl ester (3.87 g, 53%) as an off-white solid. LCMS m/z 244.14 [M+H]$^+$ @ $R_T$ 0.78 min, 89%, m/z 230.11 [Acid+H]$^+$ @ $R_T$ 1.27, 11%.

$\delta_H$ (400 MHz, (CD$_3$)$_2$SO) 11.04 (1H, s), 8.06 (1H, dd, J$_1$ 1.1, J$_2$ 8.1), 7.76-7.66 (2H, m), 7.36 (1H, td, J$_1$ 1.1, J$_2$ 7.5), 3.89 (3H, s), 2.16 (1H, m), 1.18 (4H, d, J 7.0).

Step 2

4-Chloro-2-cyclopropyl-quinoline-3-carboxylic acid ethyl ester

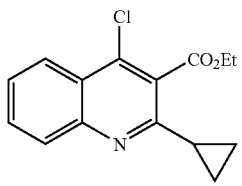

Phosphorus oxychloride (0.77 ml, 0.082 mols) was added in one portion to a suspension of 2-cyclopropyl-4-oxo-1,4-dihydro-quinoline-3-carboxylic acid ethyl ester (1.0 g, 0.041 mols) in acetonitrile and the mixture was heated at 75° C. for 90 minutes (becomes a clear solution above 65° C.). The resulting light brown solution was poured into saturated sodium bicarbonate (100 ml); the suspension was extracted with ethyl acetate and the combined organic extracts were dried and concentrated in vacuo to leave 4-Chloro-2-cyclopropyl-quinoline-3-carboxylic acid ethyl ester (1.15 g, 106%) as an off-white solid. R$_f$ (AcOEt)=0.73.

Step 3

4-(4-cyclopropyl-3-oxo-3,5-dihydro-pyrazolo[4,3-c]quinolin-2-yl)-benzoic acid

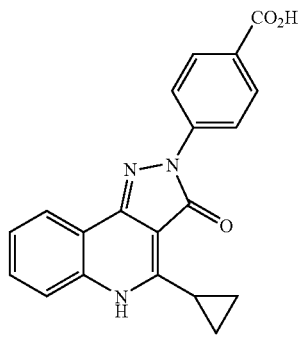

4-Chloro-2-cyclopropyl-quinoline-3-carboxylic acid ethyl ester (1.15 g, 0.0041 mols) and 4-hydrazino-benzoic acid (1.0 g, 0.0068 mols) were stirred in ethanol (30 ml) at reflux for 16 h. The bright yellow suspension was diluted with heptane, filtered, washed with cold t-butylmethyl ether and left to dry under suction to yield crude solid containing hydrazine. This solid was suspended in 1 M HCl, filtered, washed with water and then dried in vacuo to yield 4-(4-cyclopropyl-3-oxo-3,5-dihydro-pyrazolo[4,3-c]quinolin-2-yl)-benzoic acid (1.135 g, 80%) as a yellow solid, LCMS m/z 346.20 [M+H]$^+$ @ $R_T$ 1.05 min: 96% purity.

$\delta_H$ (400 MHz, (CD$_3$)$_2$SO) 11.4 (1H, s), 8.43 (2H, d, J 8.1), 8.21 (1H, dd, J$_1$ 1.2, J$_2$ 8.1), 8.07 (2H, d, J 8.1), 7.92 (1H, d, J 8.1), 7.67 (1H, t, J 6.6), 7.52 (1H, t, J 6.5), 3.43 (1H, m), 1.59 (2H, m), 1.43 (2H, m).

Step 4

4-(4-cyclopropyl-3-oxo-3,5-dihydro-pyrazolo[4,3-c]-quinolin-2-yl)-benzoyl chloride

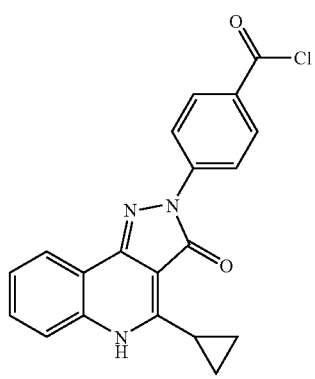

To a suspension of finely ground 4-(4-cyclopropyl-3-oxo-3,5-dihydro-pyrazolo[4,3-c]quinolin-2-yl)-benzoic acid (0.19 g. 0.55 mmol) in dichloromethane (4 ml) was added oxalyl chloride (1.6 ml, 0.01 mol) followed by a drop of dimethyl formamide. The mixture was stirred under nitrogen at 45° C. for 8 h. The solvent was removed in vacuo to yield 4-(4-cyclopropyl-3-oxo-3,5-dihydro-pyrazolo[4,3-c]quinolin-2-yl)-benzoyl chloride as a pale yellow solid, LCMS m/z [M+MeOH—Cl]$^+$ @ $R_T$ 1.46 min: 95% purity. Used without further purification.

Step 5

N-(3-Dimethylamino propyl)-4-(4-cyclopropyl-3-oxo-3,5-dihydro-pyrazolo[4,3-c]quinolin-2-yl]-benzamide

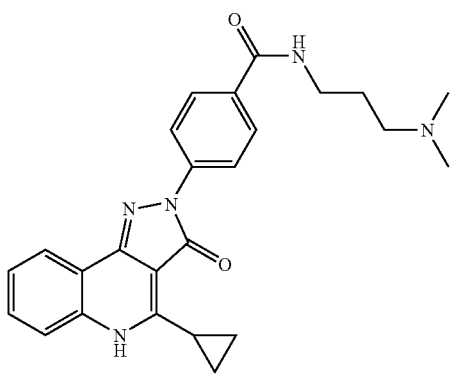

To a partial solution of 4-(4-cyclopropyl-3-oxo-3,5-dihydro-pyrazolo[4,3-c]quinolin-2-yl)-benzoyl chloride (0.1 g, 0.28 mmol) in tetrahydrofurane (6 ml) under nitrogen was added a solution of 3-dimethylamino-propyl amine (0.03 g, 0.3 mmol) in tetrahydrofurane (3 ml). The mixture was stirred at RT for 3 h. The solvent was removed under reduced pressure and the yellow solid was washed with a little saturated sodium bicarbonate, water and dried under vacuo to yield N-(3-Dimethylamino propyl)-4-(4-cyclopropyl-3-oxo-3,5-dihydro-pyrazolo[4,3-c]-quinolin-2-yl]-benzamide (57 mg, 47%) as a yellow solid. LCMS m/z 430.11 [M+H]$^+$ @ R$_T$ 0.99 min: 100% purity.

Activity ***

Preparation of Intermediate 5

4-(6-Fluoro-3-oxo-3,5-dihydro-pyrazolo[4,3-c]quinolin-2-yl]-benzoyl chloride

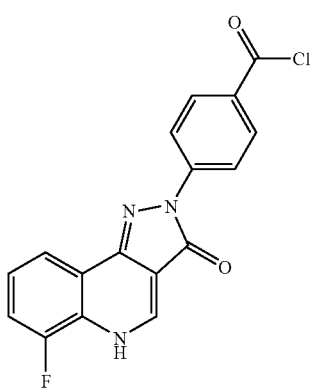

To a suspension of finely ground 4-(6-Fluoro-3-oxo-3,5-dihydro-pyrazolo[4,3-c]quinolin-2-yl]-benzoic acid (1.1 g. 3.4 mmol) in dichloromethane (6 ml) was added oxalyl chloride (2.4 ml, 29 mmol) followed by a drop of dimethyl formamide. The mixture was stirred under nitrogen at 45° C. for 3 h. The solvent was removed in vacuum to yield 4-(6-Fluoro-3-oxo-3,5-dihydro-pyrazolo[4,3-c]quinolin-2-yl]-benzoyl chloride (1.15 g, quantitative) as a pale yellow solid that was used without further purification.

EXAMPLE 66

N-(3-Dimethylamino propyl)-4-(6-fluoro-3-oxo-3,5-dihydro-pyrazolo[4,3-c]quinolin-2-yl]-benzamide hydrochloride

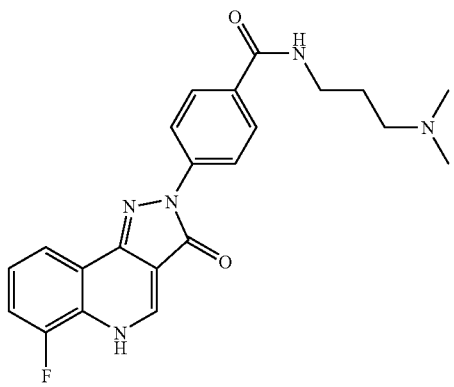

To a partial solution of 4-(6-Fluoro-3-oxo-3,5-dihydro-pyrazolo[4,3-c]quinolin-2-yl]-benzoyl chloride (0.1 g, 0.3 mmol) in tetrahydrofurane (5 ml) under nitrogen was added a solution of 3-dimethylamino-propyl amine (0.03 g, 0.3 mmol) in tetrahydrofurane. The mixture was stirred at rt for 90 minutes. The solvent was removed under reduced pressure and the yellow solid was purified via FCC silica gel (gradient elution, MeOH:H$_2$O, Fluka C$_{18}$ reverse phase) to yield N-(3-Dimethylamino propyl)-4-(6-fluoro-3-oxo-3,5-dihydro-pyrazolo[4,3-c]quinolin-2-yl]-benzamide hydrochloride (70 mg, 53%) as a yellow solid.

LCMS m/z 408.39 [M+H]$^+$ @ R$_T$ 0.89 min: 90% purity.

Activity ***

Exmaples 67-141 were prepared analogously from the appropriate benzoyl chloride and the appropriate amine

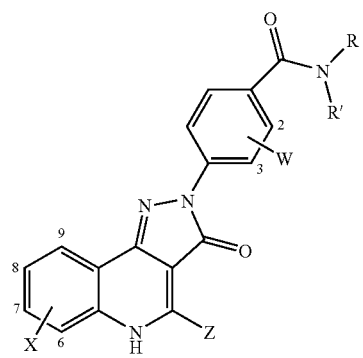

| Example | X | Z | W | R | R' | M.S. (MH+) | Activity |
|---|---|---|---|---|---|---|---|
| 67 | 6-F | H | H | —CH₂CH₂CH₂CH₂CH₂— | | 391.3 | ** |
| 68 | 6-F | H | H | —CH₂Phenyl | H | 413.2 | *** |
| 69 | 6-F | H | H | —CH₂Phenyl | Me | 427.3 | ** |
| 70 | 6-F | H | H | —CH₂CH₂OMe | H | 381.2 | *** |
| 71 | 6-F | H | H | —CH₂CH₂N(Me)₂ | H | 394.3 | *** |
| 72 | 6-F | H | H | —CH₂CO₂Me | H | 395.3 | *** |
| 73 | 6-F | H | H | —CH₂CH₂CH₂OMe | H | 395.2 | *** |
| 74 | 6-F | H | H | —CH₂CH₂CH₂N(Me)₂ | H | 408.3 | *** |
| 75 | 6-F | H | H | CH₂CH₂-(cyclohexenyl) | H | 431.3 | ** |
| 76 | 6-F | H | H | CH₂-cyclohexyl | H | 419.2 | ** |
| 77 | 6-F | H | H | Et | H | 351.2 | *** |
| 78 | 6-F | H | H | Et | Et | 379.3 | ** |
| 79 | 6-F | H | H | trans-4-aminocyclohexyl | H | 420.4 | *** |
| 80 | 6-F | H | H | —CH₂CH₂CH₂N(Me)₂ | Me | 422.4 | *** |
| 81 | 6-F | H | H | —CH2CH2CH2CH2N(Me)2 | H | 422.4 | *** |
| 82 | 6-F | H | H | —(CH₂)₄-pyrrolidinyl | H | 448.5 | *** |
| 83 | 6-F | H | H | —(CH₂)₃-pyrrolidinyl | H | 434.4 | *** |
| 84 | 6-F | H | H | —(CH₂)₃-(4-benzylpiperazinyl) | H | 525.3 | *** |
| 85 | 6-F | H | H | —CH₂CH₂CH₂CH₂CH₂N(Me)₂ | H | 450.3 | *** |
| 86 | H | H | H | —CH₂CH₂CH₂N(Me)₂ | H | 390.2 | *** |

-continued
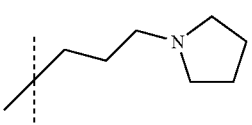
| Example | X | Z | W | R | R' | M.S. (MH+) | Activity |
|---|---|---|---|---|---|---|---|
| 87 | H | H | H | —CH₂CH₂CH₂CH₂CH₂N(Me)₂ | H | 432.1 | ** |
| 88 | H | H | H | —CH₂CH₂CH₂CH₂N(Et)₂ | H | 432.2 | ** |
| 89 | H | H | H | —CH₂CH₂CH₂N(Me)₂ | Me | 404.2 | ** |
| 90 | 6-F | H | 2-Cl | —CH₂CH₂CH₂N(Me)₂ | H | 442.1 | ** |
| 91 | H | H | H | 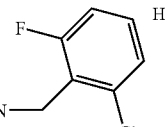 | H | 416.1 | ** |
| 92 | H | H | H | 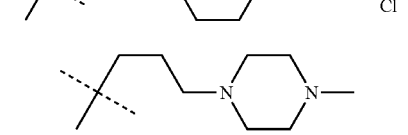 | H | 573.0 | ** |
| 93 | H | H | H | 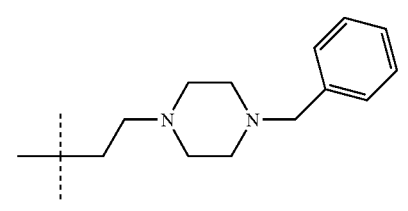 | H | 445.1 | ** |
| 94 | H | H | H | 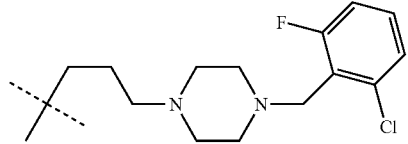 | H | 507.1 | ** |
| 95 | 6-F | H | H | 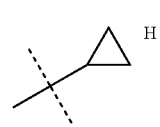 | H | 591.0 | *** |
| 96 | H | 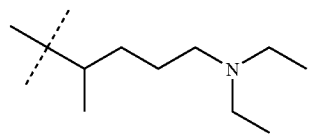 | H | —CH₂CH₂CH₂N(Me)₂ | H | 430.1 | *** |
| 97 | 6-F | H | H | (structure) | H | 464.1 | *** |

-continued

| Example | X | Z | W | R | R' | M.S. (MH+) | Activity |
|---|---|---|---|---|---|---|---|
| 98 | 6-F | H | H | -CH₂C(CH₃)₂CH₂-N(piperazine-N-Me) | H | 463.1 | *** |
| 99 | 6-F | H | 3-Cl | -(CH₂)₄-pyrrolidine | H | 482.1 | ** |
| 100 | 6-F | H | 2-Cl | -CH₂C(CH₃)₂CH₂-N(piperazine-N-Me) | H | 497.1 | ** |
| 102 | 6-F | H | 2-Cl | —CH₂CH₂CH₂CH₂N(Et)₂ | H | 484.1 | ** |
| 103 | 6-F | H | 3-Cl | —CH₂CH₂CH₂N(Me)₂ | H | 442.1 | ** |
| 104 | H | 1-methylcyclopropyl | H | -(CH₂)₄-pyrrolidine | H | 470.4 | *** |
| 105 | 6-F | H | H | piperazinyl-CH₂-(4-Cl-phenyl) | | 516.3 | * |
| 106 | 6-F | H | H | -CH₂C(CH₃)₂CH₂-N(Me)(Ph) | H | 470.3 | *** |
| 107 | 6-F | H | H | —CH₂CH₂N(iPr)₂ | H | 451.4 | *** |
| 108 | 6-F | H | 2-Cl | -(CH₂)₄-(2-methylpiperidin-1-yl) | H | 496.2 | ** |

-continued
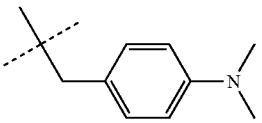
| Example | X | Z | W | R | R' | M.S. (MH+) | Activity |
|---|---|---|---|---|---|---|---|
| 109 | 6-F | H | H | 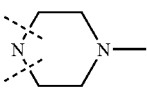 | H | 456.1 | *** |
| 110 | 6-F | H | 2-Cl | —CH$_2$CH$_2$CH$_2$CH$_2$N(Me)$_2$ | H | 456.1 | ** |
| 111 | 6-F | H | H | 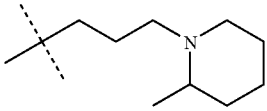 | | 406.2 | ** |
| 112 | 6-F | H | H | 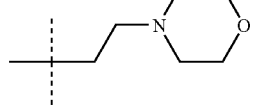 | H | 462.1 | *** |
| 113 | 6-F | H | H | 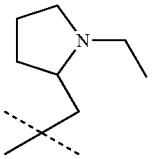 | H | 436.1 | *** |
| 114 | 6-F | H | H | 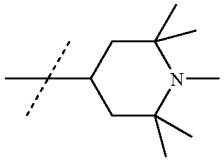 | H | 434.4 | *** |
| 115 | 6-F | H | H | 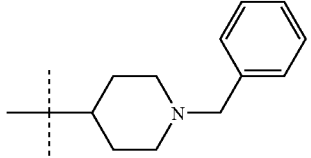 | H | 476.1 | *** |
| 116 | 6-F | H | H | 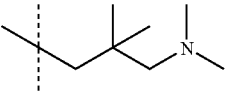 | H | 496.1 | *** |
| 117 | 6-F | H | H |  | H | 436.3 | *** |

-continued
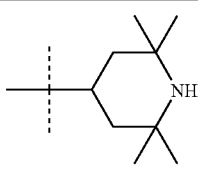
| Example | X | Z | W | R | R' | M.S. (MH+) | Activity |
|---|---|---|---|---|---|---|---|
| 118 | 6-F | H | H | 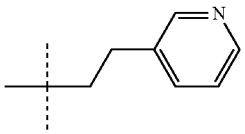 | H | 462.3 | *** |
| 119 | 6-F | H | H | 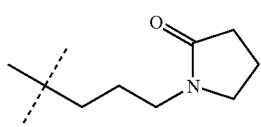 | H | 428.1 | ** |
| 120 | 6-F | H | H | —CH$_2$CH$_2$SEt | H | 411.3 | *** |
| 121 | 6-F | H | H | 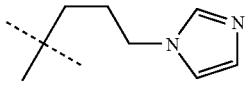 | H | 448.3 | ** |
| 122 | 6-F | H | H | 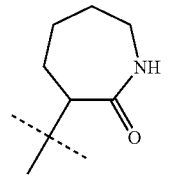 | H | 431.3 | *** |
| 123 | 6-F | H | H | 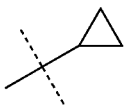 | H | 434.3 | ** |
| 124 | 6-F | H | H | —CH$_2$CH$_2$CH$_2$N(Et)$_2$ | H | 450.4 | *** |
| 125 | 6-F | 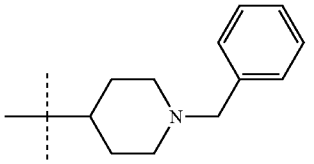 | H | 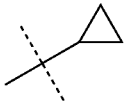 | H | 536.1 | *** |
| 126 | 6-F | 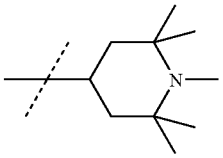 | H | 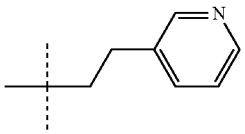 | H | 516.2 | *** |

-continued
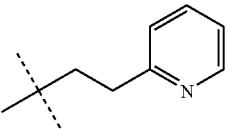
| Example | X | Z | W | R | R' | M.S. (MH+) | Activity |
|---|---|---|---|---|---|---|---|
| 127 | 6-F | H | H | 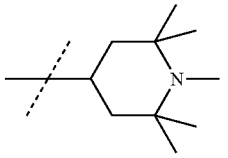 | H | 428.3 | * |
| 128 | 6-F | H | H | —CH$_2$CH$_2$CH$_2$SMe | H | 411.3 | ** |
| 129 | H | 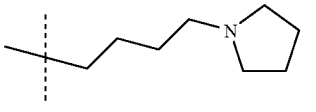 | H | 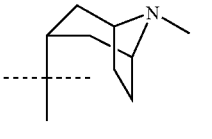 | H | 498.5 | *** |
| 130 | 6-F | 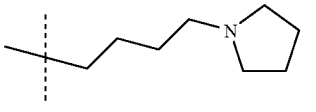 | H |  | H | 488.4 | *** |
| 131 | 6-F | H | H | 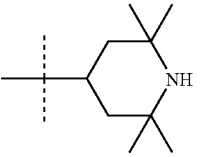 | H | 446.3 | *** |
| 132 | 6-F | 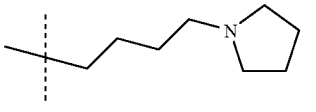 | H | —CH$_2$CH$_2$CH$_2$N(Me)$_2$ | H | 448.2 | *** |
| 133 | 6-F | 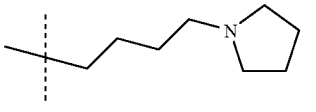 | H | 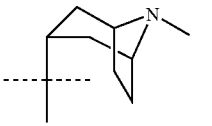 | H | 502.3 | *** |
| 134 | 6-F | 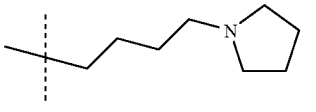 | H | 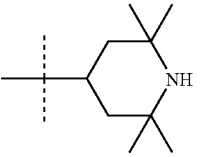 | H | 486.3 | *** |

-continued
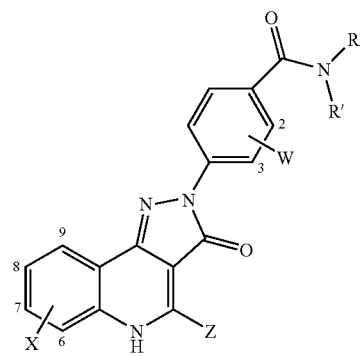
| Example | X | Z | W | R | R' | M.S. (MH+) | Activity |
|---|---|---|---|---|---|---|---|
| 135 | 6-F | cyclopropyl | H | —CH₂CH₂CH₂CH₂N(Et)₂ | H | 490.3 | *** |
| 136 | 6-F | cyclopropyl | H | 4-(N-Boc)piperidinyl | H | 546.2 | ** |
| 137 | 6-F | cyclopropyl | H | propyl-piperazinyl-CH₂-(2-F,6-Cl-phenyl) | H | 631.2 | *** |
| 138 | 6-F | cyclopropyl | H | —CH₂CH₂-(2-pyridyl) | H | 468.2 | ** |
| 139 | 6-F | cyclopropyl | H | —CH₂CH₂-(3-pyridyl) | H | 468.2 | * |
| 140 | 6-F | cyclopropyl | H | —C(CH₃)₂CH₂N(CH₃)₂ | H | 476.2 | *** |
| 141 | 6-F | cyclopropyl | H | —CH₂CH₂CH₂CH₂-pyrrolidinyl | H | 474.3 | *** |

EXAMPLE 142

{3-[4-(6-Fluoro-3-oxo-3,5-dihydro-pyrazolo[4,3-c]quinolin-2-yl)-phenyl]-ureido} acetic acid ethyl ester

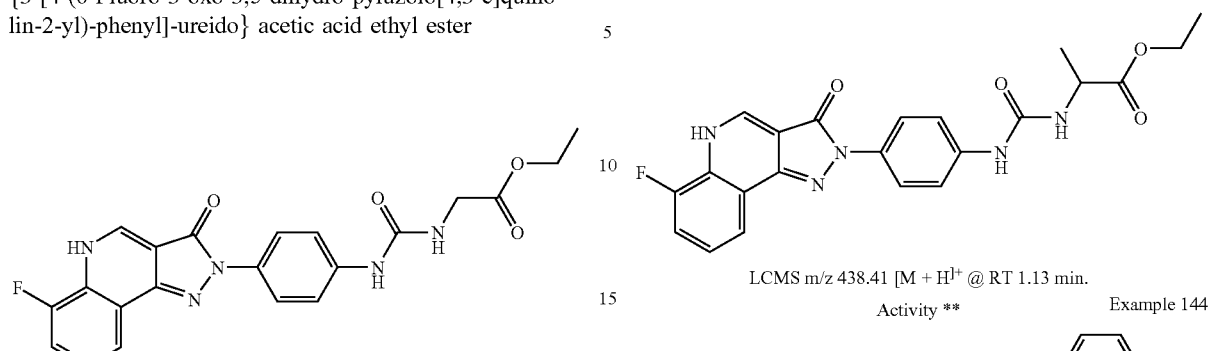

Ethyl cyanatoacetate (31 mg, 0.24 mmol) was added in one portion to a stirred solution of 2-(4-aminophenyl)-6-fluoro-2,5-dihydropyrazolo[4,3-c]quinolin-3-one (intermediate 2) (50 mg, 0.17 mmol) in N,N-dimethylformamide (2 ml) and the mixture stirred at room temperature for 16 h. Water (1 ml) was then added to the mixture to precipitate a solid, which was filtered, washed with water (1 ml) and then ethyl acetate (1 ml) and finally dried by suction to leave the urea as a yellow solid, LCMS m/z 424.40 [M+H]$^+$ @ R$_T$ 1.06 min.

Activity ***

EXAMPLES 143 AND 144

Example 143

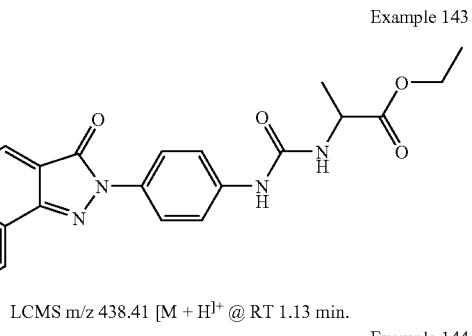

LCMS m/z 438.41 [M + H]$^+$ @ RT 1.13 min.

Activity **

Example 144

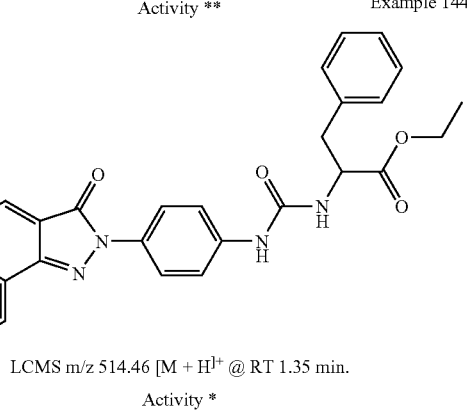

LCMS m/z 514.46 [M + H]$^+$ @ RT 1.35 min.

Activity *

The following compounds were synthesised by the method of Example 142, substituting the appropriate isocyanate, isothiocyanate or chloroformate for ethyl cyanatoacetate.

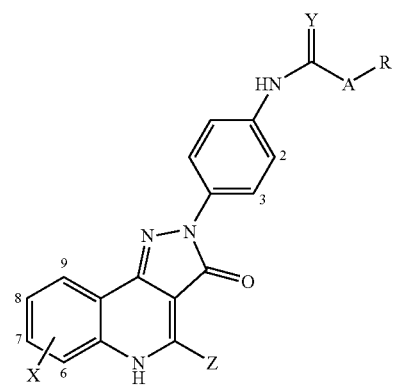

| Example | X | Z | Y | R | A | M.S. (MH+) | Activity |
|---------|-----|---|---|-----|----|--------|-----|
| 144 | 6-F | H | O | iPr | NH | 380.3 | *** |
| 145 | 6-F | H | O | nPr | NH | 380.3 | *** |
| 146 | 6-F | H | O | tBu | NH | 394.4 | *** |
| 147 | 6-F | H | O | Ph | NH | 414.3 | ** |
| 148 | 6-F | H | S | ⟨cyclopropyl-dimethyl⟩ | NH | 394.3 | ** |

-continued

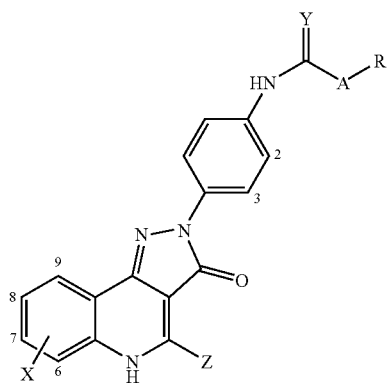

| Example | X | Z | Y | R | A | M.S. (MH+) | Activity |
|---|---|---|---|---|---|---|---|
| 149 | 6-F | H | S | (cyclohexyl-C(CH3)2-) | NH | 436.4 | * |
| 150 | 6-F | H | O | tBu | O | 395.3 | *** |
| 151 | 6-F | H | O | Et | O | 367.2 | ** |
| 152 | 6-F | H | O | CH$_2$CH$_2$N(Me)$_2$ | O | 410.2 | *** |
| 153 | H | (cyclopropyl-C(CH3)-) | O | Me | O | 375.3 | ** |
| 154 | 6-F | H | O | CH$_2$CH$_2$CH$_2$N(Me)$_2$ | O | 424.1 | *** |
| 155 | 6-F | H | O | (1-benzylpiperidin-4-yl-C(CH3)2-) | O | 512.3 | ** |
| 156 | 6-F | H | S | nPentyl | NH | 424.4 | ** |
| 157 | 6-F | H | S | CH(CH$_3$)CH(CH$_3$)CH$_3$ | NH | 424.4 | ** |
| 158 | 6-F | H | O | CH$_2$CH$_2$CH$_2$N(Et)$_2$ | NH | 465.4 | *** |
| 159 | H | H | O | nPr | NH | 362.3 | *** |
| 160 | H | H | S | (cyclopropyl-C(CH3)2-) | NH | 376.1 | ** |
| 161 | 6-F | H | O | CH$_2$CH$_2$CH$_2$N(Me)$_2$ | NH | 423.3 | *** |
| 162 | H | H | O | (CH(iPr)C(O)OMe) | NH | 434.5 | *** |
| 163 | 6-F | H | O | CH$_2$CH$_2$CH$_2$N(Me)$_2$ | NH | 437.2 | *** |
| 164 | 6-F | H | O | (C(CH3)2(CH2)4-pyrrolidinyl) | NH | 463.5 | *** |

Intermediate 6: Preparation of Methyl 4-oxothiochromane-3-carboxylate

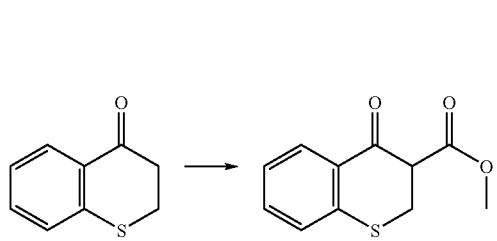

Dry tetrahydrofuran (60 ml) was cooled under nitrogen atmosphere to −50 to −60° C. 1M Lithium bis(trimethylsily)amide solution in hexane (56 ml, 56 mmol) was added. The temperature was kept at −50 to −60° C. and thiochroman-4-one was added dropwise over 20 min. Stirring was continued at low temperature for 60 min. Methyl cyanoformate (4.84 ml, 60.9 mmol) was added dropwise over 5 min to the reaction mixture. The obtained suspension was stirred at −50 to −60° C. for 80 min and then allowed to warm up to room temperature. Saturated ammonium chloride solution (100 ml) was added. The phases were separated, the aqueous phase extracted with ethyl acetate (2×100 ml). The combined organic phases were washed with water (50 ml), dried over magnesium sulphate, filtered and concentrated under vacuum. An orange oil was obtained and purified by column chromatography. The title compound was isolated as a yellow solid (4.70 g, 21.1 mmol, 42%). LCMS: m/z 221 [M−H]$^+$.

Intermediate 7: Preparation of 4-(3-Oxo-3a,4-dihydro-3H-thiochromeno[4,3-c]pyrazol-2-yl)-benzoic Acid

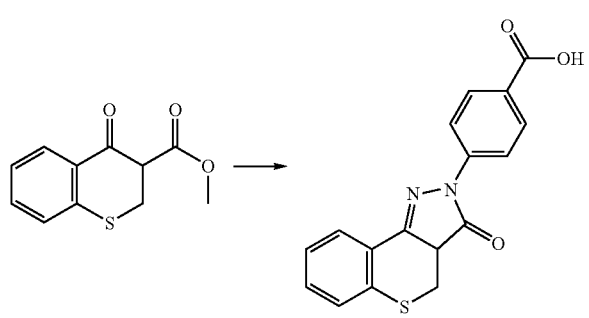

4-Oxothiochromane-3-carboxylate (0.50 g, 2.25 mmol) and hydrazinobenzoic acid (0.377 g, 2.48 mmol) were mixed in acetic acid (6 ml). The mixture was heated to reflux for 30 min. Excess acetic acid was distilled off to give a brown oil. Diethylether was added, a precipitate formed which was collected by filtration and dried under vacuum. The crude product was isolated as a red/brown solid (797 mg). LCMS: m/z 325 [M+H]$^+$. No purification was carried out.

Intermediate 8: Preparation of 4-(3-oxothiochromeno[4,3-c]pyrazol-2(3H)-yl)benzoic Acid

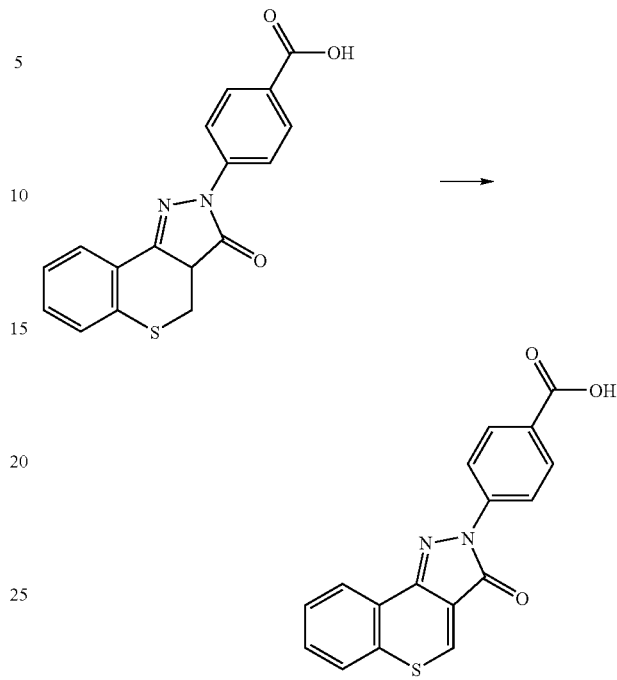

Crude 4-(3-Oxo-3a,4-dihydro-3H-thiochromeno[4,3-c]pyrazol-2-yl)-benzoic acid (250 mg, 0.77 mmol) was dissolved in dimethyl sulphoxide (6 ml). O-Chloranil (189 mg, 0.77 mmol) was added and the mixture was stirred at room temperature overnight. Water (20 ml) was added and the solids were collected by filtration and washed with water. The filter cake was triturated with toluene, filtered and dried under vacuum. The title compound was isolated as a dark brown solid (230 mg, 0.71 mmol, 92%). LCMS: m/z 323 [M+H]$^+$ Alternatively crude 4-(3-Oxo-3a,4-dihydro-3H-thiochromeno[4,3-c]pyrazol-2-yl)-benzoic acid can be stirred in dimethyl sulphoxide under exposure to air. It was found that air oxidation provides clean product, however the reaction is much slower.

EXAMPLE 165

Preparation of N-[3-(dimethylamino)propyl]-4-(3-oxothiochromeno[4,3-c]pyrazol-2(3H)-yl)benzamide

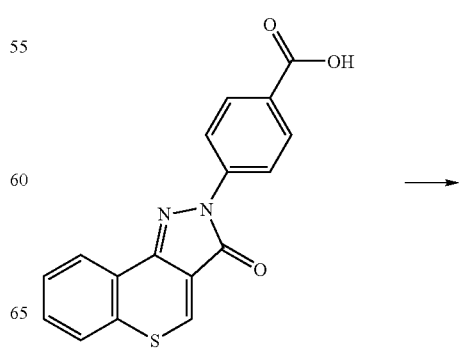

-continued

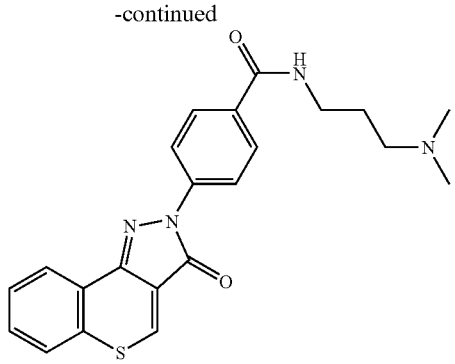

4-(3-oxothiochromeno[4,3-c]pyrazol-2(3H)-yl)benzoic acid (55 mg, 0.17 mmol) was suspended in anhydrous dimethyl acetamide (1 ml). Diisopropyl-ethyl amine (46.5 mg, 0.36 mmol, 62 µl) was added followed by 3-dimethylaminopropylamine (17.5 mg, 0.17 mmol) and [(benzotriazol-1-yloxy)-dimethylamino-methylene]-dimethyl-ammonium hexafluoro phosphate (65 mg, 0.17 mmol). The mixture was stirred at room temperature for 4 h and was purified by preparative HPLC. The title compound was isolated as a brown solid. LCMS: m/z 407 [M+H]$^+$ Activity **

EXAMPLE 166

Preparation of N-[(cyclohexylamino)propyl]-4-(3-oxothiochromeno[4,3-c]pyrazol-2(3H)-yl)benzamide

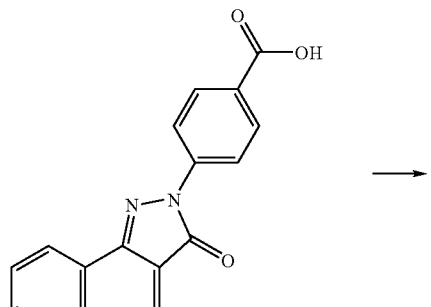

The reaction was carried out as described above. LCMS: m/z 461 [M+H]$^+$

Activity ***

EXAMPLE 167

Preparation of N-(pyrrolidin-1-yl-butyl)-4-(3-oxothiochromeno[4,3-c]pyrazol-2(3H)-yl)benzamide

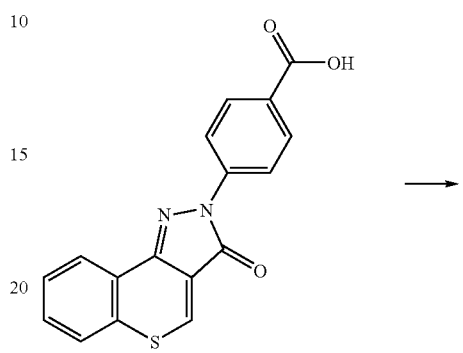

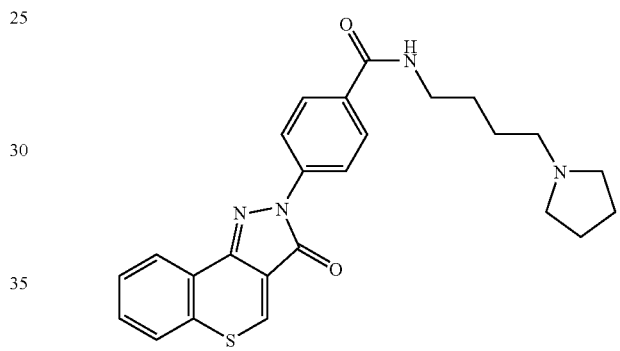

The reaction was carried out as described above. LCMS: m/z 447 [M+H]$^+$

Activity *

EXAMPLE 168

Preparation of 4-(3-oxothiochromeno[4,3-c]pyrazol-2(3H)-yl)-N-1,2,2,6,6-pentamethylpiperidin-4-ylbenzamide -continued

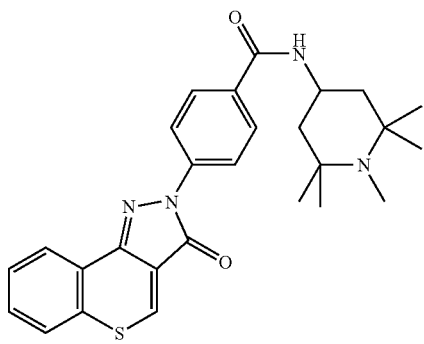

The reaction was carried out as described above. LCMS: m/z 475 [M+H]+

Activity **

Intermediate 9: Preparation of 3-[(2-fluorophenyl)sulfanyl]propanoic Acid

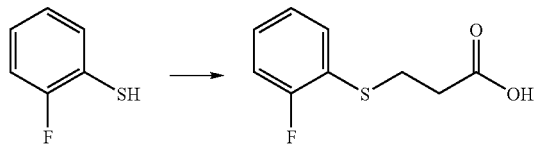

2-Fluorothiophenol (5.0 g, 39 mmol) was dissolved in tetrahydrofuran (50 ml) under a nitrogen atmosphere. Triethylamine (3.94 g, 5.33 ml, 85.8 mmol) was added. Acrylic acid (2.81 g, 2.67 ml, 39 mmol) was dissolved in tetrahydrofuran and added dropwise to the reaction solution over 2 h at room temperature. The mixture was stirred at room temperature overnight. 1M Hydrochloric acid (50 ml) was added and the phases were separated. The aqueous phase was washed with ethyl acetate (2×50 ml). The combined organic phases were dried over magnesium sulphate, filtered and concentrated under vacuum. A yellow oil was obtained which solidified upon storage at room temperature. The solid was triturated with hexane, filtered and dried under vacuum. The title compound was isolated as an off-white solid (4.19 g, 20.9 mmol, 54%).

Intermediate 10: Preparation of 8-fluoro-2,3-dihydro-4H-thiochromen-4-one

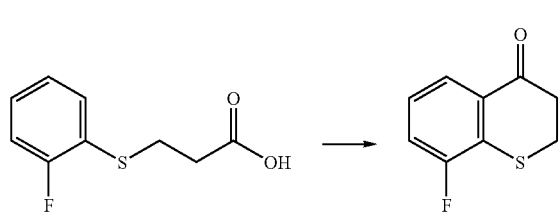

3-[(2-Fluorophenyl)sulfanyl]propanoic acid (4.0 g, 20 mmol) was mixed with concentrated sulphuric acid (20 ml) at 0-5° C. The reaction solution was stirred at 0 to 5° C. for 3 h then allowed to warm up to room temperature overnight. The mixture was quenched dropwise into ice to give a white suspension. The aqueous phase was extracted with ethyl acetate (1×200 ml, 1×100 ml). The combined organic phases were washed with saturated sodium bicarbonate solution (1×50 ml), water (1×50 ml), 1M hydrochloric acid (50 ml) and water (2×50 ml). The organic phase was dried over magnesium sulphate, filtered and concentrated under vacuum. The title compound was isolated as a yellow solid (2.10 g, 11.5 mmol, 58%).

Intermediate 11: Preparation of methyl 8-fluoro-4-oxothiochromane-3-carboxylate

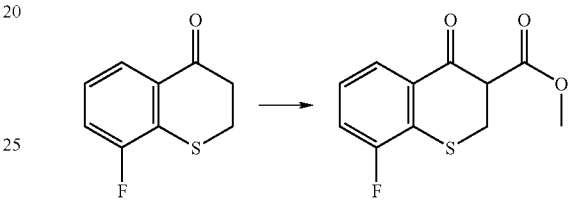

1M Lithium hexamethyldisilazide solution in hexane (13.2 ml) was dissolved in anhydrous tetrahydrofuran (20 ml) under nitrogen atmosphere. The solution was cooled to −78° C. 8-Fluoro-2,3-dihydro-4H-thiochromen-4-one (2.00 g, 11 mmol) was dissolved in tetrahydrofuran (40 ml), the solution was transferred to the dropping funnel and added dropwise over 30 min to the reaction mixture maintaining the temperature below −60° C. An orange clear solution was obtained which was stirred at −78° C. to −65° C. for 2 h. Methyl cyanoformate (0.935 g, 0.87 ml) was dissolved in tetrahydrofuran (2 ml) and added dropwise to the reaction solution. Stirring was continued at low temperature for 1 h, the mixture was then allowed to warm to room temperature. Saturated ammonium chloride solution (20 ml) and water (10 ml) were added, the phases mixed for 5 min and separated. The aqueous phase was washed with ethyl acetate (2×100 ml) and the combined organic phases were dried over magnesium sulphate. The mixture was filtered and the solvent removed under vacuum to give an orange oil. The crude oil was purified by column chromatography; mobile phase: hexanes, gradient to hexanes/ethyl acetate [90:10]. The title compound was isolated as a yellow solid (1.19 g, 4.95 mmol, 45%).

Intermediate 12: Preparation of 4-(6-fluoro-3-oxothiochromeno[4,3-c]pyrazol-2(3H)-yl)benzoic Acid

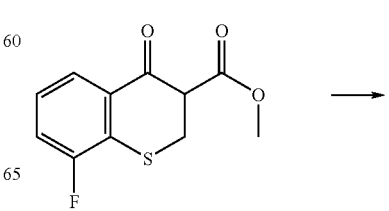

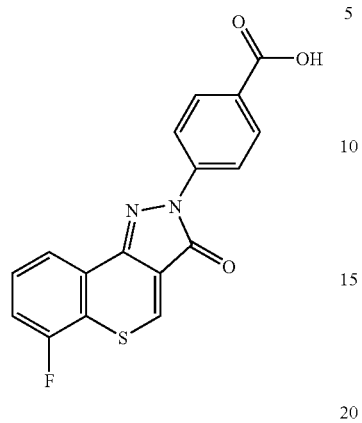

Methyl 8-fluoro-4-oxothiochromane-3-carboxylate (1.19 g, 4.95 mmol) and 4-hydrazinobenzoic acid (755 mg, 4.95 mmol) were mixed with glacial acetic acid (10 ml). The mixture was heated to reflux for 4 h. Excess acetic acid was removed under vacuum to give an orange oil. Ethyl acetate (10 ml) was added and the mixture sonicated. Precipitation of an orange solid was observed. The solids were collected by filtration and washed with ethyl acetate. The filter cake was taken up in dimethyl suphoxide (10 ml) and air-oxidised at room temperature for one week. Water (20 ml) was added to the reaction mixture, the solids were collected by filtration, slurried in ethyl acetate, filtered and dried under vacuum. The title compound was isolated as an orange powder (175 mg, 0.51 mmol, 10%). LCMS: m/z 341.

EXAMPLE 169

Preparation of N-[3-(dimethylamino)propyl]-4-(6-fluoro-3-oxothiochromeno[4,3-c]pyrazol-2(3H)-yl)benzamide

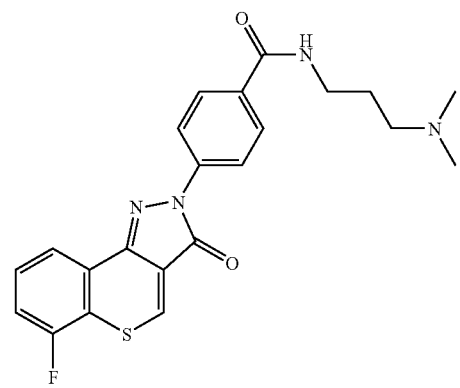

4-(6-Fluoro-3-oxothiochromeno[4,3-c]pyrazol-2(3H)-yl) benzoic acid (41 mg, 0.12 mmol) was dissolved in anhydrous dimethyl-acetamide (1 ml). Diisopropyl-ethyl amine (46 mg, 0.36 mmol, 62 µl) was added followed by [(benzotriazol-1-yloxy)-dimethylamino-methylene]-dimethyl-ammonium hexafluoro phosphate (65 mg, 0.17 mmol) and 3-dimethylaminopropylamine (12 mg, 0.12 mmol). The mixture was stirred at room temperature overnight and purified by preparative HPLC. The title compound was isolated as a brown solid. LCMS: m/z 425 [M+H]+.

Activity **

EXAMPLE 170

Preparation of N-[(cyclohexylamino)propyl]-4-(6-fluoro-3-oxothiochromeno[4,3-c]pyrazol-2(3H)-yl)benzamide

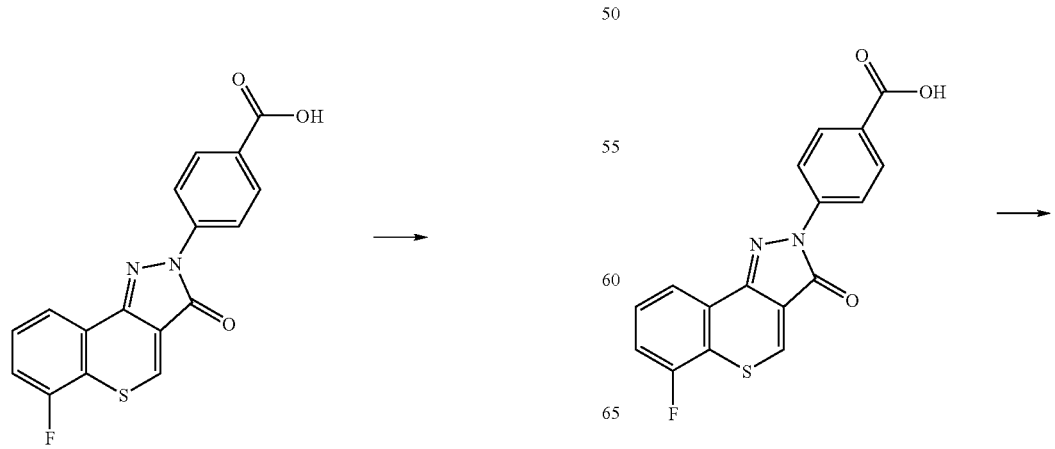

-continued

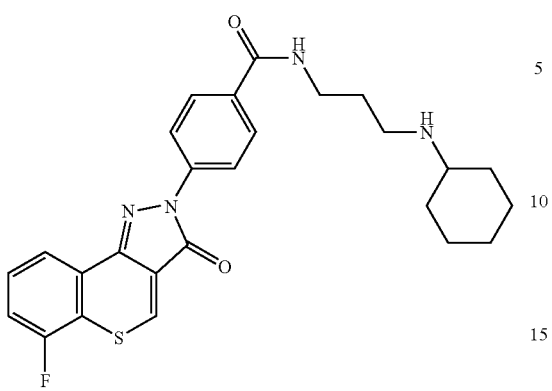

The reaction was carried out as described above. LCMS: m/z 479 [M+H]⁺.

Activity **

EXAMPLE 171

Preparation of N-(pyrrolidin-1-yl-butyl)-4-(6-fluoro-3-oxothiochromeno[4,3-c]pyrazol-2(3H)-yl)benzamide

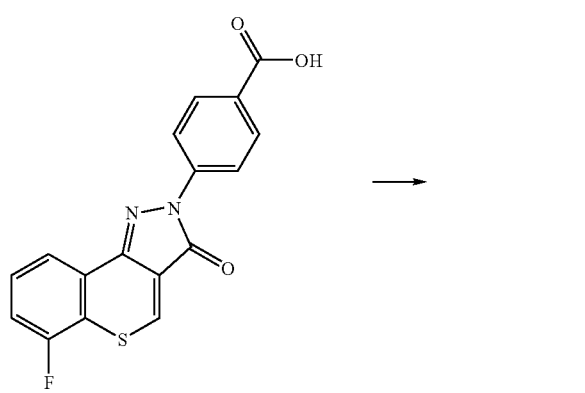

The reaction was carried out as described above. LCMS: m/z 465 [M+H]⁺.

Activity ***

EXAMPLE 173

Preparation of 4-(6-fluoro-3-oxothiochromeno[4,3-c]pyrazol-2(3H)-yl)-N-1,2,2,6,6-pentamethylpiperidin-4-ylbenzamide

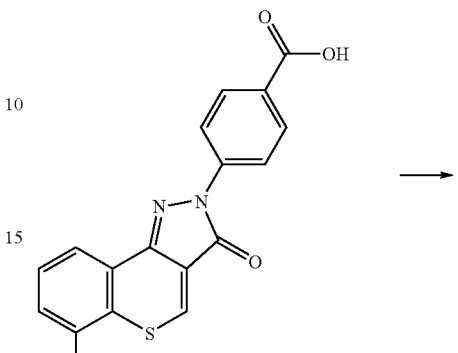

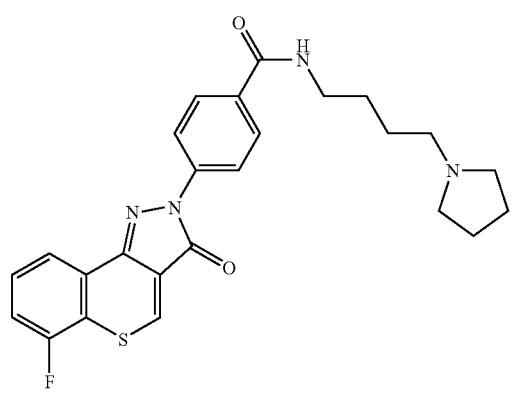

The reaction was carried out as described above. LCMS: m/z 493 [M+H]⁺

Activity ***

Assay Section

The examples described above were tested in a cell free Homogenous Time Resolved Fluorescence (HTRF) assay to determine their activity as inhibitors of the CD80-CD28 interaction.

In the assay, europium and allophycocyanin (APC) are associated with CD28 and CD80 indirectly (through antibody linkers) to form a complex, which brings the europium and APC into close proximity to generate a signal. The complex comprises the following six proteins: fluorescent label 1, linker antibody 1, CD28 fusion protein, CD80 fusion protein, linker antibody 2, and fluorescent label 2. The table below describes these reagents in greater detail.

| | |
|---|---|
| Fluorescent label 1 | Anti-Rabbit IgG labelled with Europium (1 μg/ml) |
| Linker antibody 1 | Rabbit IgG specific for mouse Fc fragment (3 μg/ml) |
| CD28 fusion protein | CD28 - mouse Fc fragment fusion protein (0.48 μg/ml) |
| CD80 fusion protein | CD80 mouse Fab fragment (C215) fusion protein (1.9 μg/ml) |
| Linker antibody 2 | GαMκ-biotin: biotinylated goat IgG specific for mouse kappa chain (2 μg/ml) |
| Fluorescent label 2 | SA-APC: streptavidin labelled allophycocyanin (8 μg/ml) |

On formation of the complex, europium and APC are brought into proximity and a signal is generated.

Non-specific interaction was measured by substituting a mouse Fab fragment (C215) for the CD80 mouse Fab fragment fusion protein (1.9 µg/ml). The assay was carried out in black 384 well plates in a final volume of 30 µl. Assay buffer: 50 mM Tris-HCl, 150 mM NaCl pH7.8, containing 0.1% BSA (w/v) added just prior to use.

Compounds were added to the above reagents in a concentration series ranging between 100 µM-1.7 nM. The reaction was incubated for 4 hours at room temperature. Dual measurements were made using a Wallac Victor 1420 Multilabel Counter. First measurement: excitation 340 nm, emission 665 nm, delay 50 µs, window time 200 µs. second measurement: excitation 340 nm, emission 615 nm, delay 50 µs, window time 200 µs. Counts were automatically corrected for fluorescence crossover, quenching and background.

By way of illustration, the $EC_{50}$ results for the compounds of Examples 15, 21, 29, 35 and 83 were 8 µM, 1.9 µM, 950 nM, 148 nM and 90 nM respectively. For convenience, the EC50 activities of compounds tested are recorded above in summary form as:

EC50: *=>10 µM, =1-10 µM, *=<1 µM.

The invention claimed is:

1. A compound of formula (I) or a pharmaceutically or veterinarily acceptable salt thereof:

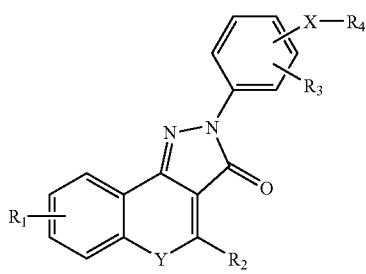

wherein
$R_1$ and $R_3$ independently represent H; F; Cl; Br; —$NO_2$; —CN; $C_1$-$C_6$ alkyl optionally substituted by F or Cl; or $C_1$-$C_6$ alkoxy optionally substituted by F;
$R_2$ represents H, or optionally substituted $C_1$-$C_6$ alkyl, $C_3$-$C_7$ cycloalkyl or optionally substituted phenyl;
Y represents —O—, —S—, N-oxide, or —N($R_5$)— wherein $R_5$ represents H or $C_1$-$C_6$ alkyl;
X represents a bond or a divalent $C_1$-$C_6$ alkylene radical;
$R_4$ represents —$NR_7$C(=O)$R_6$, —$NR_7$C(=O)O$R_6$, —NHC(=O)NH$R_6$ or —NHC(=S)NH$R_6$ wherein:
when $R_4$ represents —$NR_7$C(=O)$R_6$ or —$NR_7$C(=O)O$R_6$, $R_6$ represents H, or a radical of formula —(Alk)$_b$-Q wherein b is 0 or 1 and Q represents H; —$CF_3$; —OH; —SH; —$NR_8R_8$ wherein each $R_8$ may be the same or different; an ester group; or an optionally substituted phenyl, $C_3$-$C_7$ cycloalkyl, $C_5$-$C_7$ cycloalkenyl or heterocyclic ring having from 5 to 8 ring atoms;
when $R_4$ represents —NHC(=O)NH$R_6$ or —NHC(=S)NH$R_6$, $R_6$ represents a radical of formula —(Alk)$_b$-Q wherein b is 1 and Q represents —$CF_3$; —OH; —SH; —$NR_8R_8$ wherein each $R_8$ may be the same or different; an ester group; or an optionally substituted phenyl, $C_3$-$C_7$ cycloalkyl, $C_5$-$C_7$ cycloalkenyl or heterocyclic ring having from 5 to 8 ring atoms;

where Alk is a divalent straight chain or branched $C_1$-$C_{12}$ alkylene, $C_2$-$C_{12}$ alkenylene or $C_2$-$C_{12}$ alkynylene radical which may be interrupted by one or more non-adjacent —O—, —S— or —N($R_8$)— radicals wherein $R_8$ represents H or $C_1$-$C_4$ alkyl, $C_3$-$C_4$ alkenyl, $C_3$-$C_4$ alkynyl, or $C_3$-$C_6$ cycloalkyl, and
$R_7$ represents H or $C_1$-$C_6$ alkyl; or when taken together with the atom or atoms to which they are attached $R_6$ and $R_7$ form an optionally substituted heterocyclic ring having from 5 to 8 ring atoms.

2. A compound as claimed in claim 1 wherein $R_1$ is H, F, Cl, methyl or methoxy.

3. A compound as claimed in claim 1 wherein $R_2$ is H, methyl, cyclopropyl, phenyl, or fluoro-, chloro-, methyl-, or methoxy-substituted phenyl.

4. A compound as claimed in claim 1 wherein $R_3$ is H, F, Cl, methyl, or methoxy.

5. A compound as claimed in claim 1 wherein Y is —O—, —S—, or —N($R_5$)— wherein $R_5$ represents H or methyl.

6. A compound as claimed in claim 1 wherein X is a bond, or a —$CH_2$— or —$CH_2CH_2$— radical.

7. A compound as claimed in claim 1 wherein $R_4$ represents —$NR_7$C(=O)$R_6$, —$NR_7$C(=O)O$R_6$, —NHC(=O)NH$R_6$ or —NHC(=S)NH$R_6$ wherein:
when $R_4$ represents —$NR_7$C(=O)$R_6$ or —$NR_7$C(=O)O$R_6$, $R_6$ is H or a radical of formula —Alk$_b$-Q wherein b is 0 or 1 and
Alk is a —($CH_2$)$_n$—, —CH(($CH_2$)$_m$$CH_3$)($CH_2$)$_n$—, —CH(($CH_2$)$_m$$CH_3$)(($CH_2$)$_p$$CH_3$)($CH_2$)$_n$—, —($CH_2$)$_n$—O—($CH_2$)$_m$—, or —($CH_2$)$_n$—O—($CH_2$)$_n$—O—($CH_2$)$_m$—, radical where n is 1, 2, 3 or 4 and m and p are independently 0, 1, 2, 3 or 4, and Q represents H, —OH, —COOCH$_3$, phenyl, cyclopropyl, cyclopentyl, cyclohexyl, pyridyl, furyl, thienyl, or oxazolyl, and
when $R_4$ represents —NHC(=O)NH$R_6$ or —NHC(=S)NH$R_6$, $R_6$ is a radical of formula —Alk$_b$-Q wherein b is 1 and
Alk is a —($CH_2$)$_n$—, —CH(($CH_2$)$_m$$CH_3$)($CH_2$)$_n$—, —CH(($CH_2$)$_m$$CH_3$)(($CH_2$)$_p$$CH_3$)($CH_2$)$_n$—, —($CH_2$)$_n$—O—($CH_2$)$_m$—, or —($CH_2$)$_n$—O—($CH_2$)$_n$—O—($CH_2$)$_m$—, radical, where n is 1, 2, 3 or 4 and m and p are independently 0, 1, 2, 3 or 4, and Q represents —OH, —COOCH$_3$, phenyl, cyclopropyl, cyclopentyl, cyclohexyl, pyridyl, furyl, thienyl, or oxazolyl, and
$R_7$ is H, or when taken together with the nitrogen atom to which they are attached $R_6$ and $R_7$ form a pyrrolidine-2-one or pyrrolidine-2,5-dione ring.

8. A compound as claimed in claim 1 wherein $R_1$ is H, F, or Cl; $R_2$ is H; $R_3$ is H, F, or Cl; Y is —NH—; X is a bond; and $R_4$ represents —$NR_7$C(=O)$R_6$, —$NR_7$C(=O)O$R_6$ or —NHC(=O)NH$R_6$ wherein:
when $R_4$ represents —$NR_7$C(=O)$R_6$ or —$NR_7$C(=O)O$R_6$, $R_6$ is H or a radical of formula —Alk$_b$-Q wherein b is 0 or 1 and
Alk is a —($CH_2$)$_n$—, —CH(($CH_2$)$_m$$CH_3$)($CH_2$)$_n$—, —CH(($CH_2$)$_m$$CH_3$)(($CH_2$)$_p$$CH_3$)($CH_2$)$_n$—, —($CH_2$)$_n$—O—($CH_2$)$_m$—, or —($CH_2$)$_n$—O—($CH_2$)$_n$—O—($CH_2$)$_m$—, radical where n is 1, 2, 3 or 4 and m and p are independently 0, 1, 2, 3 or 4, and Q represents H, —OH, —COOCH$_3$, phenyl, cyclopropyl, cyclopentyl, cyclohexyl, pyridyl, furyl, thienyl, or oxazolyl, and
when $R_4$ represents —NHC(=O)NH$R_6$, $R_6$ is a radical of formula —Alk$_b$-Q wherein b is 1 and
Alk is a —($CH_2$)$_n$—, —CH(($CH_2$)$_m$$CH_3$)($CH_2$)$_n$—, —CH(($CH_2$)$_m$$CH_3$)(($CH_2$)$_p$$CH_3$)($CH_2$)$_n$—, —($CH_2$)$_n$—O—($CH_2$)$_m$—, or —($CH_2$)$_n$—O—($CH_2$)$_n$—O—($CH_2$)$_m$—, radical where n is 1, 2, 3 or 4 and m and p are independently 0, 1, 2, 3 or 4, and Q represents —OH, —COOCH$_3$, phenyl, cyclopropyl, cyclopentyl, cyclohexyl, pyridyl, furyl, thienyl, or oxazolyl, and R$_7$ is H, or when taken together with the nitrogen atom to which they are attached R$_6$ and R$_7$ form a pyrrolidine-2-one or pyrrolidine-2,5-dione ring.

9. A compound as claimed in claim 1 wherein R$_1$ is F, R$_2$ is H or cyclopropyl, R$_3$ is H, X is a bond, and R$_4$ is —NR$_7$C(=O)R$_6$, or —NHC(=O)NHR$_6$, wherein:

when R$_4$ represents —NR$_7$C(=O)R$_6$, R$_6$ is H or a radical of formula —Alk$_b$-Q wherein b is 0 or 1 and Alk is a —(CH$_2$)$_n$—, —CH((CH$_2$)$_m$CH$_3$)(CH$_2$)$_n$—, —CH((CH$_2$)$_m$CH$_3$)((CH$_2$)$_p$CH$_3$)(CH$_2$)$_n$—, —(CH$_2$)$_n$—O—(CH$_2$)$_m$—, or —(CH$_2$)$_n$—O—(CH$_2$)$_n$—O—(CH$_2$)$_m$—, radical where n is 1, 2, 3 or 4 and m and p are independently 0, 1, 2, 3 or 4, and Q represents H, —OH, —COOCH$_3$, phenyl, cyclopropyl, cyclopentyl, cyclohexyl, pyridyl, furyl, thienyl, or oxazolyl, and when R$_4$ represents —NHC(=O)NHR$_6$, R$_6$ is a radical of formula —Alk$_b$-Q wherein b is 1 and Alk is a —(CH$_2$)$_n$—, —CH((CH$_2$)$_m$CH$_3$)(CH$_2$)$_n$—, —CH((CH$_2$)$_m$CH$_3$)((CH$_2$)$_p$CH$_3$)(CH$_2$)$_n$—, —(CH$_2$)$_n$—O—(CH$_2$)$_m$—, or —(CH$_2$)$_n$—O—(CH$_2$)$_n$—O—(CH$_2$)$_m$—, radical where n is 1, 2, 3 or 4 and m and p are independently 0, 1, 2, 3 or 4, and Q represents —OH, —COOCH$_3$, phenyl, cyclopropyl, cyclopentyl, cyclohexyl, pyridyl, furyl, thienyl, or oxazolyl.

10. A pharmaceutical or veterinary composition comprising a compound as claimed in claim 1 together with a pharmaceutically or veterinarily acceptable excipient or carrier.

11. A compound as claimed in claim 2 wherein R$_2$ is H, methyl, cyclopropyl, phenyl, or fluoro-, chloro-, methyl-, or methoxy-substituted phenyl.

12. A compound as claimed in claim 2 wherein R$_3$ is H, F, Cl, methyl, or methoxy.

13. A compound as claimed in claim 3 wherein R$_3$ is H, F, Cl, methyl, or methoxy.

14. A compound as claimed in claim 11 wherein R$_3$ is H, F, Cl, methyl, or methoxy.

15. A compound as claimed in claim 2 wherein Y is —O—, —S—, or —N(R$_5$)— wherein R$_5$ represents H or methyl.

16. A compound as claimed in claim 2 wherein X is a bond, or a —CH$_2$— or —CH$_2$CH$_2$— radical.

17. A compound as claimed in claim 2 wherein R$_4$ represents —NR$_7$C(=O)R$_6$, —NR$_7$C(=O)OR$_6$, —NHC(=O)NHR$_6$ or —NHC(=S)NHR$_6$ wherein:

when R$_4$ represents —NR$_7$C(=O)R$_6$ or —NR$_7$C(=O)OR$_6$, R$_6$ is H or a radical of formula —Alk$_b$-Q wherein b is 0 or 1 and Alk is a —(CH$_2$)$_n$—, —CH((CH$_2$)$_m$CH$_3$)(CH$_2$)$_n$—, —CH((CH$_2$)$_m$CH$_3$)((CH$_2$)$_p$CH$_3$)(CH$_2$)$_n$—, —(CH$_2$)$_n$—O—(CH$_2$)$_m$—, or —(CH$_2$)$_n$—O—(CH$_2$)$_n$—O—(CH$_2$)$_m$—, radical where n is 1, 2, 3 or 4 and m and p are independently 0, 1, 2, 3 or 4, and Q represents H, —OH, —COOCH$_3$, phenyl, cyclopropyl, cyclopentyl, cyclohexyl, pyridyl, furyl, thienyl, or oxazolyl, and when R$_4$ represents —NHC(=O)NHR$_6$ or —NHC(=S)NHR$_6$, R$_6$ is a radical of formula —Alk$_b$-Q wherein b is 1 and Alk is a —(CH$_2$)$_n$—, —CH((CH$_2$)$_m$CH$_3$)(CH$_2$)$_n$—, —CH((CH$_2$)$_m$CH$_3$)((CH$_2$)$_p$CH$_3$)(CH$_2$)$_n$—, —(CH$_2$)$_n$—O—(CH$_2$)$_m$—, or —(CH$_2$)$_n$—O—(CH$_2$)$_n$—O—(CH$_2$)$_m$—, radical where n is 1, 2, 3 or 4 and m and p are independently 0, 1, 2, 3 or 4, and Q represents —OH, —COOCH$_3$, phenyl, cyclopropyl, cyclopentyl, cyclohexyl, pyridyl, furyl, thienyl, or oxazolyl, and R$_7$ is H, or when taken together with the nitrogen atom to which they are attached R$_6$ and R$_7$ form a pyrrolidine-2-one or pyrrolidine-2,5-dione ring.

18. A pharmaceutical or veterinary composition comprising a compound as claimed in claim 2 together with a pharmaceutically or veterinarily acceptable excipient or carrier.

19. A pharmaceutical or veterinary composition comprising a compound as claimed in claim 3 together with a pharmaceutically or veterinarily acceptable excipient or carrier.

* * * * *